US012370266B2

(12) United States Patent
Krug et al.

(10) Patent No.: US 12,370,266 B2
(45) Date of Patent: Jul. 29, 2025

(54) POLYMER COMPOSITE NANOMATERIAL ENCAPSULATION SYSTEM

(71) Applicant: Core Quantum Technologies, Inc., Columbus, OH (US)

(72) Inventors: Kristie Marie Krug, Upper Arlington, OH (US); Mythreyi Unni, Columbus, OH (US)

(73) Assignee: Core Quantum, Inc., Columbus, OH (US)

( * ) Notice: Subject to any disclaimer, the term of this patent is extended or adjusted under 35 U.S.C. 154(b) by 233 days.

(21) Appl. No.: 17/943,788

(22) Filed: Sep. 13, 2022

(65) Prior Publication Data
US 2024/0108749 A1    Apr. 4, 2024

(51) Int. Cl.
*A61K 47/69* (2017.01)
*A61K 47/68* (2017.01)
(Continued)

(52) U.S. Cl.
CPC ...... *A61K 47/6931* (2017.08); *A61K 47/6883* (2017.08); *B82Y 15/00* (2013.01); *G01N 33/5434* (2013.01); *G01N 33/56972* (2013.01)

(58) Field of Classification Search
CPC .............. A61K 9/5153; A61K 47/6931; A61K 49/0002
See application file for complete search history.

(56) References Cited

U.S. PATENT DOCUMENTS

| 6,114,038 A | 9/2000 | Castro et al. |
| 9,550,160 B2 | 1/2017 | Winter et al. |

(Continued)

FOREIGN PATENT DOCUMENTS

| CN | 116144345 | 5/2023 |
| WO | 2009/012109 A2 | 1/2009 |
| WO | 2017/201089 A1 | 11/2017 |

OTHER PUBLICATIONS

NanoOptical Materials Blue CdS/ZnS & Blue/Green CdSSe/ZnS Core Shell Quantum Dots—Water Soluble[online], [retrieved on Aug. 12, 2024], retrieved online <https://web.archive.org/web/20151120124109/https://nomcorp.com/product/blue-cdszns-bluegreen-cdssezns-core-shell-quantum-dots-water-soluble/>. (Year: 2015).*

(Continued)

*Primary Examiner* — Carlos A Azpuru
(74) *Attorney, Agent, or Firm* — Craig R. Miles; CR MILES P.C.

(57) ABSTRACT

Generally, a polymer nanomaterial encapsulation system useful in the production of polymer encapsulated nanoparticles comprised of a hydrophobic nanoparticle encapsulated in the hydrophobic region of the polymer with the external hydrophilic region of the polymer ensuring water-solubility and affording a functional group which can be utilized for the production of nanoparticle conjugates. Specifically, particular embodiments include a polymer nanoparticle structure including one or more of: a quantum dot and/or a superparamagnetic iron oxide nanoparticle and/or an upconverting nanoparticle, encapsulated in polystyrene-b-polyethylene glycol amine for the production of antibody conjugates useful in the capture of cellular targets.

53 Claims, 15 Drawing Sheets
(2 of 15 Drawing Sheet(s) Filed in Color)

(51) Int. Cl.
  *B82Y 15/00* (2011.01)
  *G01N 33/543* (2006.01)
  *G01N 33/569* (2006.01)

(56) References Cited

U.S. PATENT DOCUMENTS

| | | | |
|---|---|---|---|
| 10,873,003 | B2 | 12/2020 | Chen |
| 2006/0083781 | A1 | 4/2006 | Shastri et al. |
| 2008/0160090 | A1 | 7/2008 | Oraevsky et al. |
| 2009/0173207 | A1 | 7/2009 | Leach |
| 2010/0112716 | A1* | 5/2010 | Rosenzweig ......... B82Y 15/00 977/773 |
| 2012/0251453 | A1 | 10/2012 | Fukuda et al. |
| 2013/0039858 | A1 | 2/2013 | Brown et al. |
| 2013/0078469 | A1* | 3/2013 | Winter .................. B22F 1/056 252/301.16 |
| 2013/0195755 | A1 | 8/2013 | Poselt et al. |
| 2015/0376209 | A1 | 12/2015 | Krutak et al. |
| 2017/0087530 | A1 | 3/2017 | Winter et al. |
| 2018/0353913 | A1 | 12/2018 | Link et al. |
| 2019/0136130 | A1 | 5/2019 | Han et al. |
| 2022/0145175 | A1 | 5/2022 | Dai et al. |

OTHER PUBLICATIONS

Abdellatif AAH, Younis MA, Alsharidah M, Al Rugaie O, Tawfeek HM. Biomedical Applications of Quantum Dots: Overview, Challenges, and Clinical Potential. Int J Nanomedicine. May 2, 2022;17:1951-1970. (Year: 2022).*
Early Stage High-Content HIV Diagnosis Based on Concurrent Monitoring of Actin Cytoskeleton, CD3, CD4, and CD8 Yu Kyung Tak and Joon Myong Song Analytical Chemistry 2013 85 (9), 4273-4278 (Year: 2013).*
Chattopadhyay, P., Price, D., Harper, T. et al. Quantum dot semiconductor nanocrystals for immunophenotyping by polychromatic flow cytometry. Nat Med 12, 972-977 (2006). (Year: 2006).*
Ligand Shell Structure in Lead Sulfide—Oleic Acid Colloidal Quantum Dots Revealed by Small-Angle Scattering Michael P. Weir, et al., The Journal of Physical Chemistry Letters 2019 10 (16), 4713-4719 (Year: 2019).*
Application of star poly(ethylene glycol) derivatives in drug delivery and controlled release, Xiaobao Zhao, Jingxing Si, Dongsheng Huang, Ke Li, Ying Xin, Meihua Sui, Journal of Controlled Release,vol. 323, (2020), 565-577 (Year: 2020).*
Tomczak N, Liu R, Vancso JG. Polymer-coated quantum dots. Nanoscale. Dec. 21, 2013;5(24):12018-32 (Year: 2013).*
Jenkem Biotin PEG Succinimidyl Carboxymethyl Ester, (retrieved Aug. 26, 2024), https://web.archive.org/web/20201025162525/https://www.jenkemusa.com/product/biotin-peg-succinimidyl-carboxymethyl-ester (Year: 2020).*
NanoOptical Materials CdSe/ZnS Visible Quantum Dots—Water Soluble, (retrieved on Aug. 26, 2024), https://web.archive.org/web/20151119032744/https://nomcorp.com/product/cdsezns-visible-quantum-dots-water-soluble/ (Year: 2015).*
NanoOptical Materials Near Infrared CdSeTe/ZnS Quantum Dots—Water Soluble, (retrieved Aug. 12, 2024), https://web.archive.org/web/20151120124114/https://nomcorp.com/product/near-infrared-cdsetezns-quantum-dots-water-soluble/ (Year: 2015).*
NanoOptical Materials Cd Free Core/Shell Quantum Dots—Water Soluble, (retrieved on Aug. 12, 2024), https://web.archive.org/web/20151217011758/https://nomcorp.com/product/cd-free-coreshell-quantum-dots-water-soluble/ (Year: 2015).*
NanoOptical Materials PbS/CdS Longer Near Infrared Quantum Dots—Water Soluble, (retrieved Aug. 12, 2024), https://web.archive.org/web/20160731072433/https://nomcorp.com/product/pbscds-longer-near-infrared-quantum-dots-water-soluble/ (Year: 2016).*
PCT International Patent Application No. PCT/US23/30594, International Search Report and Written Opinion of the International Searching Authority dated Mar. 15, 2024, 20 pages.
Chinnathambi et al. "Biocompatible CdSe/ZnS quantum dot micelles for long-term cell imaging without alteration to the native structure of the blood plasma protein human serum albumin." RSC Adv., 2017, 7:2392-2402.
BioParticles. "PbS/CdS Quantum Dots." Nov. 7, 2020, downloaded from the URL: <https://www.cd-bioparticles.con/product/pbs-cds-quantum-dots-list-208.html> on Dec. 20, 2023, 1 page.
Lee et al. "Electrohydrodynamic Mixing-Mediated Nanoprecipitation for Polymer Nanoparticle Synthesis." ACS Appl. Poly. Mater., 2019, 1:691-700.
BioLegend. "Monoclonal Mouse Anti-Human CD3 Antibody (for Flow Cytometry) from BioLegend (Clone HIT3a)." May 2016, downloaded from the URL: <https://www.biocompare.com/Product-Reviews/185878-Monoclonal-mouse-Anti-human-CD3-antibody-for-flow-cytometry-from-BioLegend-clone-HIT3a/> on Dec. 20, 2023, 3 pages.
RNDSystems. "Human CD4 Alexa Fluor® 405-conjugated Antibody." 2017, downloaded from the URL: <https://www.rndsystems.com/product/human-cd4-alexa-fluor-405-conjugated-antibody-11830_fab3791v#product-datesheets> on Dec. 20, 2023, 3 pages.
Weir et al. "Ligand Shell Structure in Lead Sulfide-Oleic Acid Colloidal Quantum Dots Revealed by Small-Angle Scattering." J. Phys. Chem. Lett., Jul. 2019, 10:4713-4719.
U.S. Appl. No. 61/178,835, filed May 15, 2009, Henary et al.
PCT International Patent Application No. PCT/US20/22668, International Search Report and Written Opinion of the International Searching Authority dated Jul. 6, 2020, 11 pages.
U.S. Appl. No. 12/778,569, Office Action mailed Mar. 4, 2016.
U.S. Appl. No. 12/778,569, Office Action mailed Jul. 19, 2016.
U.S. Appl. No. 12/778,569, Office Action mailed Jun. 9, 2017.
U.S. Appl. No. 12/778,569, Notice of Allowance mailed Jun. 13, 2018.
Cooper et al. The Use of Heptamethine Cyanine Dyes as Drug-Conjugate Systems in the Treatment of Primary and Metastatic Brain Tumors. Frontiers in Oncology, Jun. 2021, vol. 11, Article 654921, 16 pages.
Fu et al. Plasmonic Enhancement of Single-Molecule Fluorescence Near a Silver Nanoparticle. J Fluoresc., Nov. 2007; 17(6):811-816.
Pham et al. Synthesis and Application of a Water-Soluble Near-Infrared Dye for Cancer Detection Using Optical Imaging. Bioconjugate Chem., Apr. 2005, 16(3):735-740.
Ali et al. Efficacy, long-term toxicity, and mechanistic studies of gold nanorods photothermal therapy of cancer in xenograft mice. Proceedings of the National Academy of Sciences, Mar. 2017, 114(15):E3110-E3118.
Alrahili et al. Absorption cross section of gold nanoparticles based on NIR laser heating and thermodynamic calculations. Scientific Reports, Nov. 2020, 10, article No. 18790.
Alrahili et al. Morphology Dependence in Photothermal Heating of Gold Nanomaterials with Near-Infrared Laser. J. Phys. Chem. C, Feb. 2020, 124(8):4755-4763.
Bevilacqua et al. Antifouling Strategies of Nanoparticles for Diagnostic and Therapeutic Application: A Systematic Review of the Literature. Nanomaterials, Mar. 2021, 11(3):780.
Chichel et al. Hyperthermia—description of a method and a review of clinical applications. Rep Pract Oncol Radiother, Oct. 2007, 12(15):267-275.
Choi et al. Heptamethine Cyanine Dye Mediated Drug Delivery: Hype or Hope. Bioconjug. Chem., Jun. 2020, 31(7):1724-1739.
Fan et al. Nanotechnology for Multimodal Synergistic Cancer Therapy. Chem. Rev., Nov. 2017, 117(22):13566-13638.
García et al. Zwitterionic-Coated "Stealth" Nanoparticles for Biomedical Applications: Recent Advances in Countering Biomolecular Corona Formation and Uptake by the Mononuclear Phagocyte System. Small, Jul. 2014 (published online Mar. 2014), 10(13):2516-2529.
Hirsch et al. Nanoshell-mediated near-infrared thermal therapy of tumors under magnetic resonance guidance. PNAS, Nov. 2003, 100(23):13549-13554.
Huang et al. Applications of gold nanorods for cancer imaging and photothermal therapy. Cancer nanotechnology. Methods Mol Biol, Jan. 2010, 624:343-357.

(56) References Cited

OTHER PUBLICATIONS

Huang et al. Folic acid-conjugated silica-modified gold nanorods for X-ray/CT imaging-guided dual-mode radiation and photothermal therapy. Biomaterials Dec. 2011, 32(36):9796-9809.

Huang et al. Plasmonic photothermal therapy (PPTT) using gold nanoparticles. Lasers in medical science, Jul. 2008 (published online Aug. 2007), 23(3):217-228.

Jauffred et al. Plasmonic Heating of Nanostructures. Chem. Rev., May 2019, 119(13):8087-8130.

Li et al. RGD-conjugated dendrimer-modified gold nanorods for in vivo tumor targeting and photothermal therapy. Molecular pharmaceutics, 2010 (published on Web Nov. 2009), 7(1):94-104.

Raoof et al. Gold Nanoparticles and Radiofrequency in Experimental Models for Hepatocellular Carcinoma. Nanomedicine, Aug. 2014, 10(6):1121-1130.

Rastinehad et al. Gold nanoshell-localized photothermal ablation of prostate tumors in a clinical pilot device study. PNAS, Sep. 2019, 116(37):18590-18596.

Savchuk et al. Size-dependent emission of a dipole coupled to a metal nanoparticle. MRS Advances, Nov. 2020, 5(62):3315-3325.

Shi et al. Heptamethine carbocyanine dye-mediated near-infrared imaging of canine and human cancers through the HIF-1$\alpha$/OATPs signaling axis. Oncotarget, Oct. 2014, 5(20):10114-26.

PubChem. Substance Record for SIDS 135686945. Available Date May 28, 2012 [retrieved on Jun. 15, 2020] from the Internet, htttps://pubchem.ncbi.nim.nih.gov/substance/135686945.

Yang et al. Near IR Heptamethine Cyanine Dye-Mediated Cancer Imaging. Clin. Cancer Res., May 2010, 16(10):2833-2844.

Lee et al. Electrohydrodynamic Mixing-Mediated Nanoprecipitation for Polymer Nanoparticle Synthesis. ACS Appl. Polym. Mater., Mar. 2019, 1(4):691-700.

\* cited by examiner

QD – QUANTUM DOT (2a)

SPION – SUPERPARAMAGNETIC IRON OXIDE NANOPARTICLES (2b)

▭ LIGAND (16)

▯ FIRST LINKER (10a)

▯ SECOND LINKER (10b)

□ AGENT

○ } HYDROPHILIC REGION
〰 } HYDROPHOBIC REGION } POLYMER (P) (3)

◎ FUNCTIONAL GROUP (9)

⊻ ANTIBODY (LINKER AND/OR AGENT) (5')

○ CELL (24, 24')

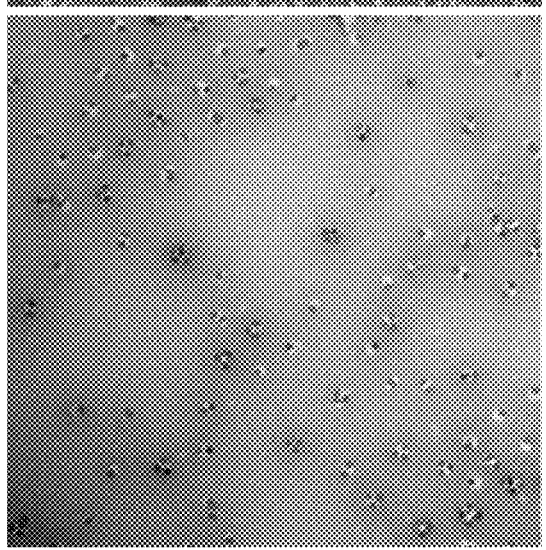
FIG. 8A PNEP-MAGDOTS 20nm
FIG. 8B PNEP-MAGDOTS 15nm
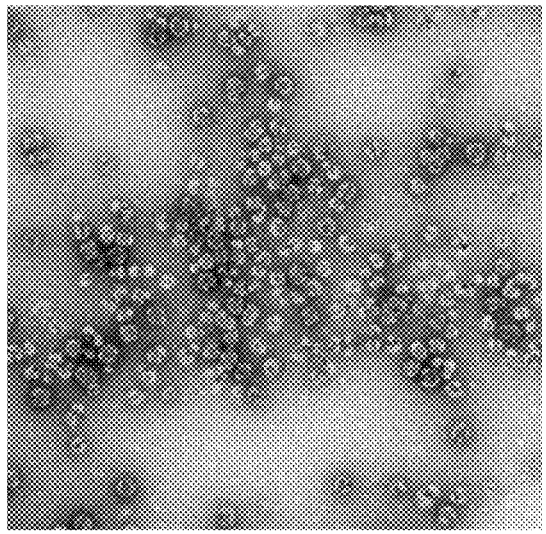
FIG. 8C PNEP-MAGDOTS 5nm

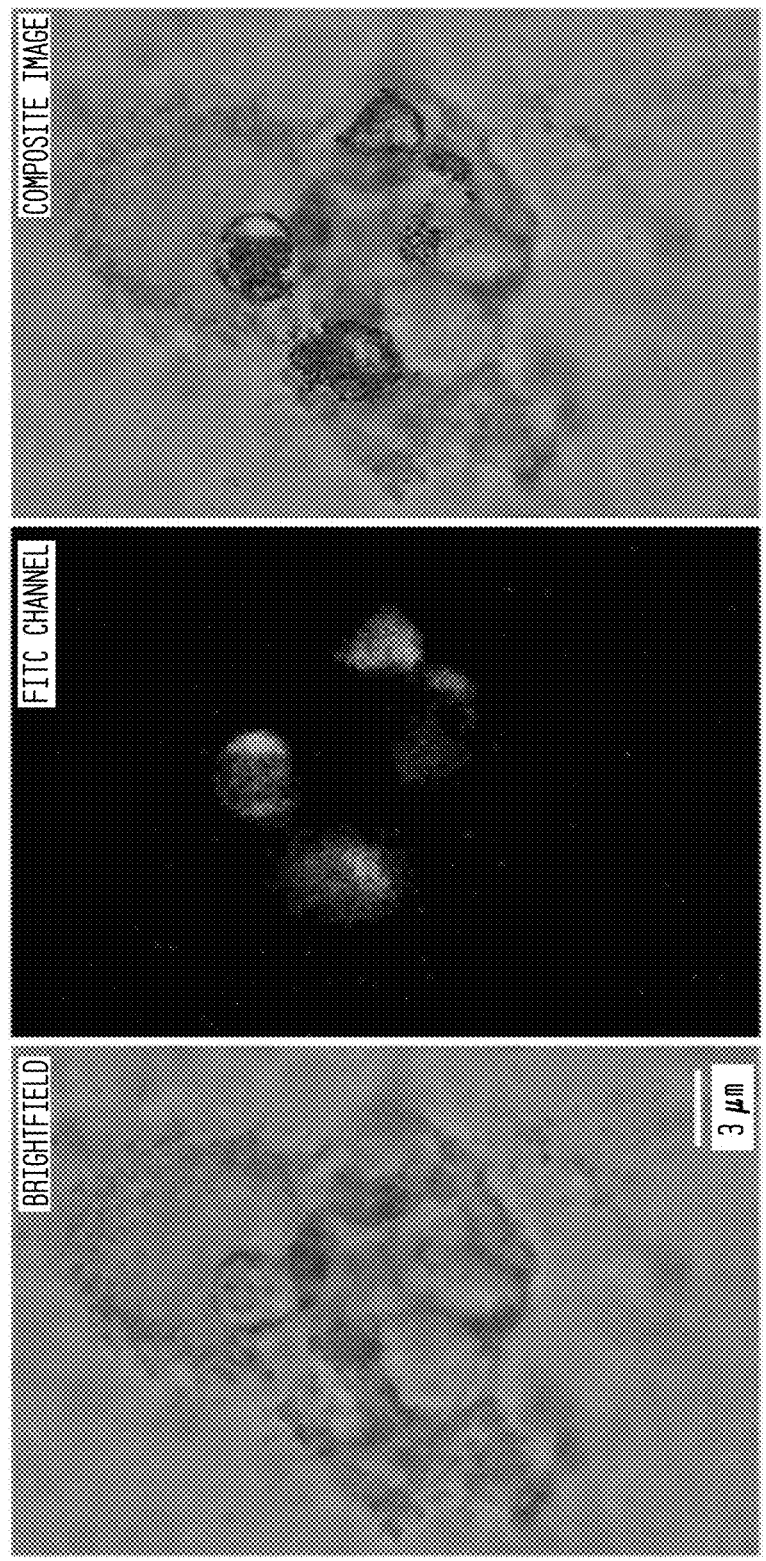

POLYMER COMPOSITE NANOMATERIAL ENCAPSULATION SYSTEM

I. FIELD OF THE INVENTION

Generally, a nanomaterial polymer encapsulation system useful in the production of nanocomposites comprising a hydrophobic nanoparticle encapsulated in a hydrophobic region of a polymer with the external hydrophilic region of the polymer ensuring water-solubility and affording a functional group which can be utilized for the production of nanocomposite conjugates.

Specifically, particular embodiments can comprise nanocomposites including one or more nanoparticles including a quantum dot ("QD") and/or a superparamagnetic iron oxide nanoparticle ("SPION") and/or an upconverting nanoparticle encapsulated in a polystyrene-b-polyethylene glycol amine ("PS-b-PEG-$NH_2$") affording an amine functional group that can be activated to conjugate antibodies, modified antibodies, or antibody fragments, and in a particular embodiments, activated with methyltetrazine polyethylene glycol-4-N-hydroxysuccinimide esters ("methyltetrazine-PEG4-NHS ester") to allow conjugation of trans-cyclooctyne ("TCO") modified antibody or antibody fragments.

II. BACKGROUND OF THE INVENTION

Nanocomposites have a diverse variety of potential applications including, but not limited to, medicine, biomedicine, biotechnology, biomaterials, biomechanics, and energy production. Current methods of polymer encapsulation of nanoparticles such as QD or SPION to produce nanocomposites have led to agglomeration of the nanocomposites limiting production to small batches, low photochemical stability, lack of uniform size and brightness, a lack of specificity of nanocomposite conjugates to cellular targets, and the lack of methodologies for rapid purification of nanocomposites bound to cellular targets. There would be substantial advantages in nanocomposites and methods of making and using nanocomposites that minimize agglomeration in large batch production, have high photochemical stability, uniform and narrow size distribution and brightness, high binding specificity to cellular targets, and protocols for rapid purification of nanocomposites bound to cellular targets.

III. SUMMARY OF THE INVENTION

A broad object of particular embodiments of the invention can be to provide a nanocomposite comprising one or more nanoparticles encapsulated by a polymer having a hydrophobic region associated with the nanoparticle and a hydrophilic region including a functional group associated with the aqueous environment, wherein the nanoparticle can comprise one or more of a QD or a SPION, and combinations thereof, and the polymer can comprise a polystyrene-b-polyethylene glycol including a functional group, wherein polystyrene can have a molecular weight occurring in the range of about 1.5 kDa to about 40 kDa, and wherein the polyethylene glycol can have a molecular weight occurring in the range of about 10 kDa to about 40 kDa, whereby combinations and permutations of the QD, SPION, molecular weight of the polystyrene and/or the molecular weight of the polyethylene glycol and selection of the branched structure of the polyethylene glycol, and variation in mass ratios thereof, allow for a numerous and wide variety of nanocomposites to be produced having substantially uniform hydrodynamic diameter occurring in a range of about 40 nm to about 500 nm and brightness due to QD having different emission wavelengths occurring in the range of 420 nm and 1000 nm.

Another broad object of particular embodiments of the invention can be to provide a QD and/or SPION nanocomposite antibody conjugate capable of specifically binding a cellular target, wherein illustrative embodiments of the nanocomposite antibody conjugate include one or more of anti-CD3 or anti-CD4 antibodies capable of specifically binding CD3 and or CD4 peripheral blood mononuclear cells.

Another broad object of particular embodiments of the invention can be to provide nanocomposites comprising polymer encapsulated QD or SPION, or combinations thereof, for specific targeting of macrophages, wherein illustrative embodiments comprise the uptake of embodiments of nanocomposites by hemocytes.

Another broad object of particular embodiments of the invention can be to provide a method of isolating QD and/or SPION nanocomposite antibody conjugates bound to cells, wherein SPION nanocomposite antibody conjugates bound to the cells can be separated and isolated by influence of a magnetic field, and wherein isolated QD or SPION nanocomposite antibody conjugates bound to cells can be analyzed by flow cytometry, and in particular embodiments the analyzed QD or SPION nanocomposite antibody conjugates bound to the cells can be flow sorted into discrete populations based on one or more characteristics of the cells.

Naturally, further objects of the invention are disclosed throughout other areas of the specification, drawings, photographs, and claims.

IV BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a block flow diagram illustrating in general overview the process to make and use elements of the nanoparticle polymer encapsulation system including: polymer synthesis, preparation of polymer encapsulated nanoparticles, antibody preparation, production of polymer encapsulated nanoparticle conjugated antibodies, and polymer encapsulated nanoparticle conjugated antibodies bound to cellular targets.

Figure 1:
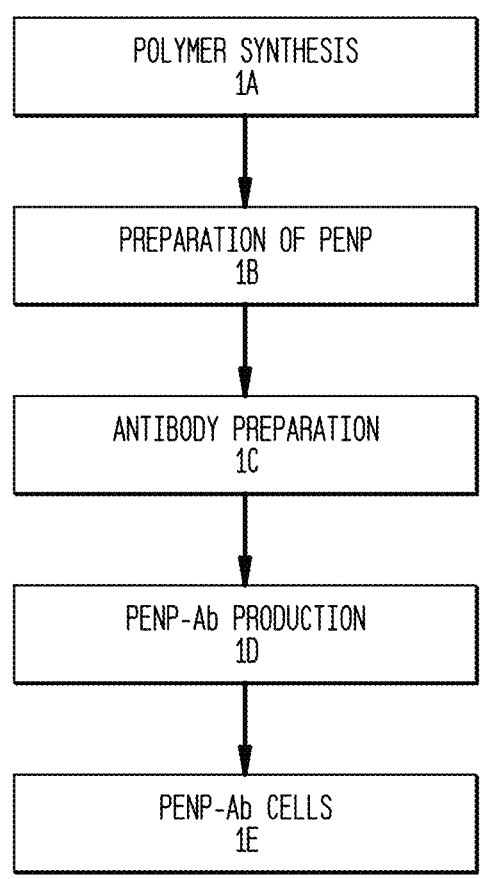
Figure 2:
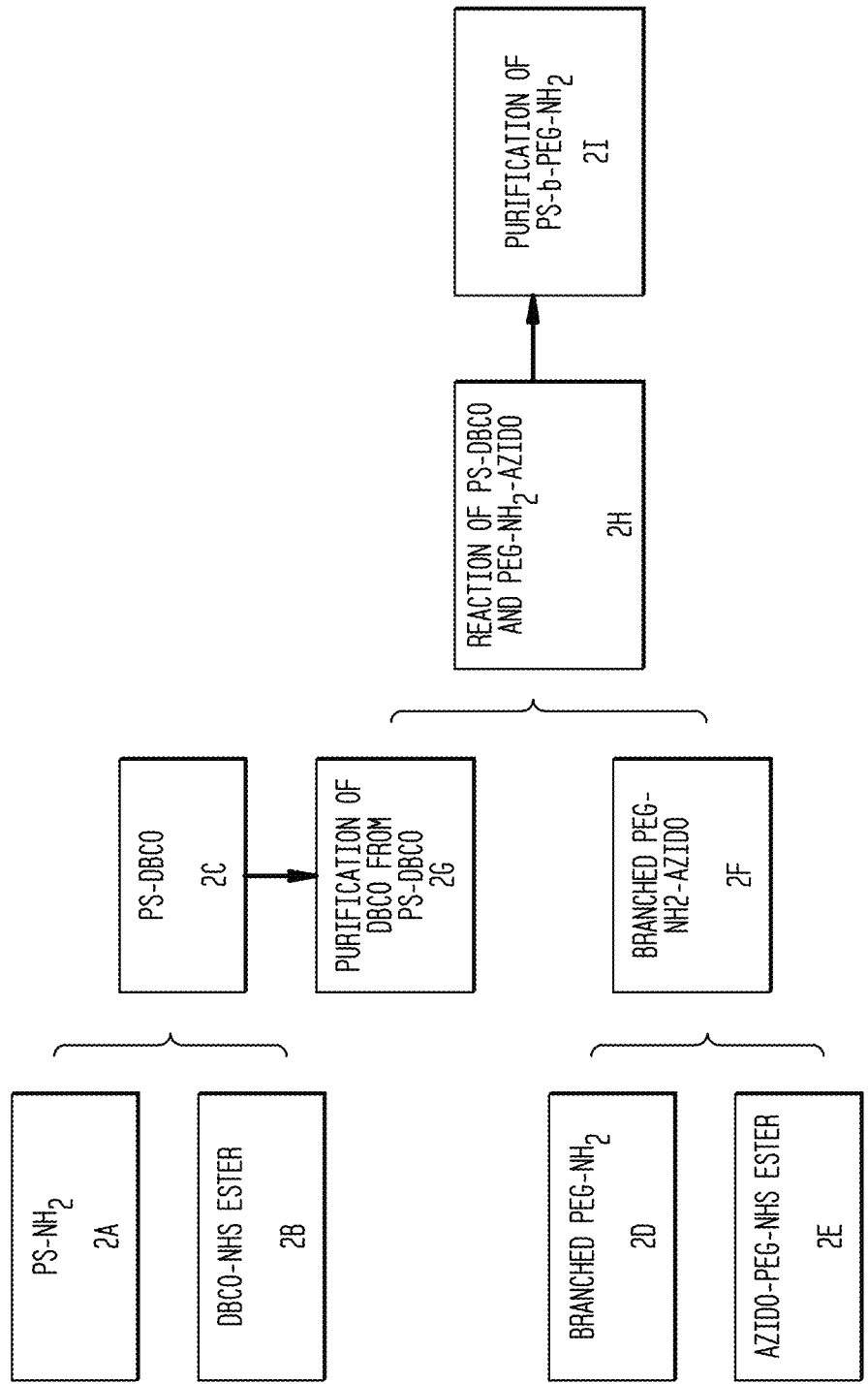
FIG. 2 is a block flow diagram including Blocks 2A through 2I illustrating a process to synthesize polymers encompassed by the method of FIG. 1, Block 1A including the illustrative example of PS-b-PEG-$NH_2$.
Figure 4A:
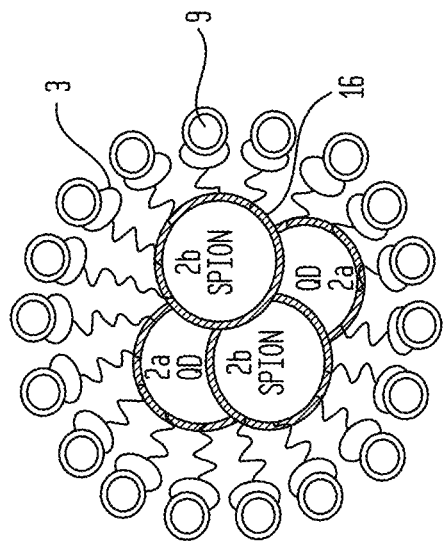
FIG. 4A illustrates an embodiment of polymer encapsulated nanoparticle encompassed by FIG. 1, Block 1B including one more QD encapsulated in a polymer obtained by the polymer synthesis process shown in FIG. 2, Blocks 2A through 2I.
Figure 4B:
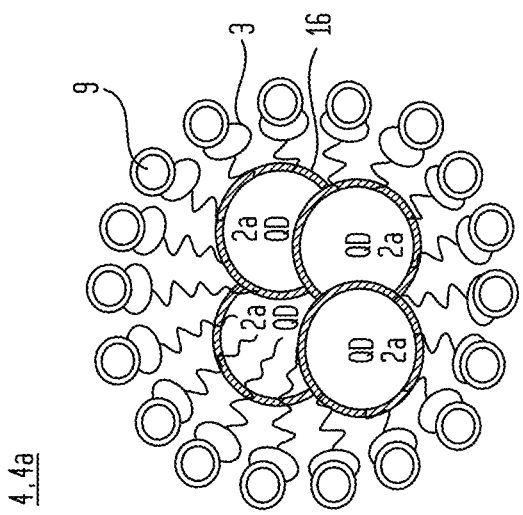
FIG. 4B illustrates an embodiment of polymer encapsulated nanoparticle encompassed by FIG. 1, Block 1B including one more QD and one or more SPION encapsulated in a polymer obtained by the polymer synthesis process shown in FIG. 2, Blocks 2A through 2I.
Figure 4C:
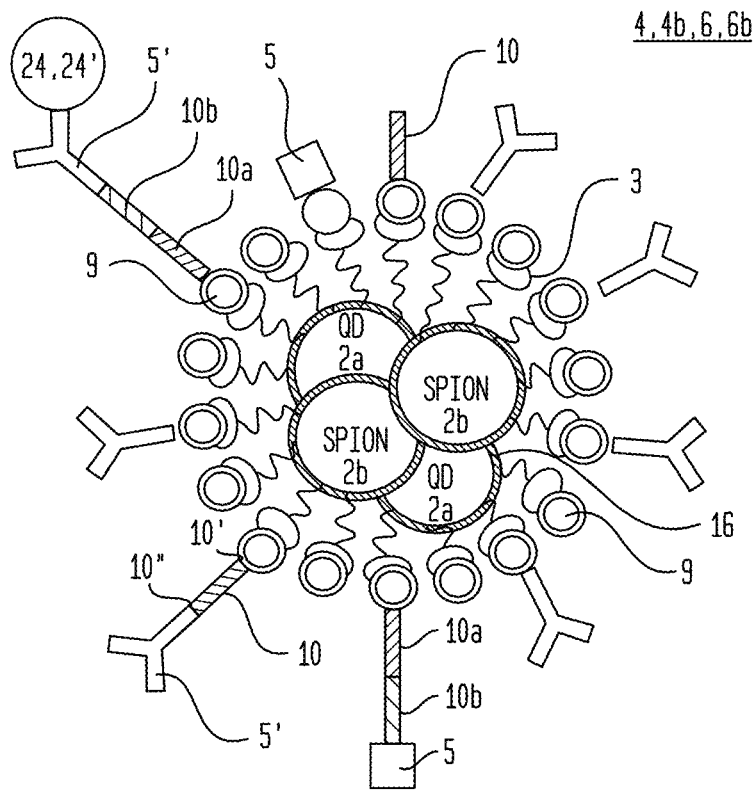

FIG. 4C illustrates an embodiment of polymer encapsulated nanoparticle encompassed by FIG. 1, Block 1B including one more QD and/or one or more SPION encapsulated in a polymer obtained by the polymer synthesis process shown in FIG. 2, Blocks 2A through 2I, wherein the polymer can have a functional group which can be activated to bind one or more agents including as illustrative examples: one or more linkers, a polyethylene glycol, a fluorescent probe, an aptamer, a vitamin, a cell surface receptor, a cell coat, a protein, a peptide, a radioactive isotope, a contrast media, a surface charge modifier, a lectin, or, an antibody, a half antibody, an antibody fragment, and combinations thereof.

Figure 5:
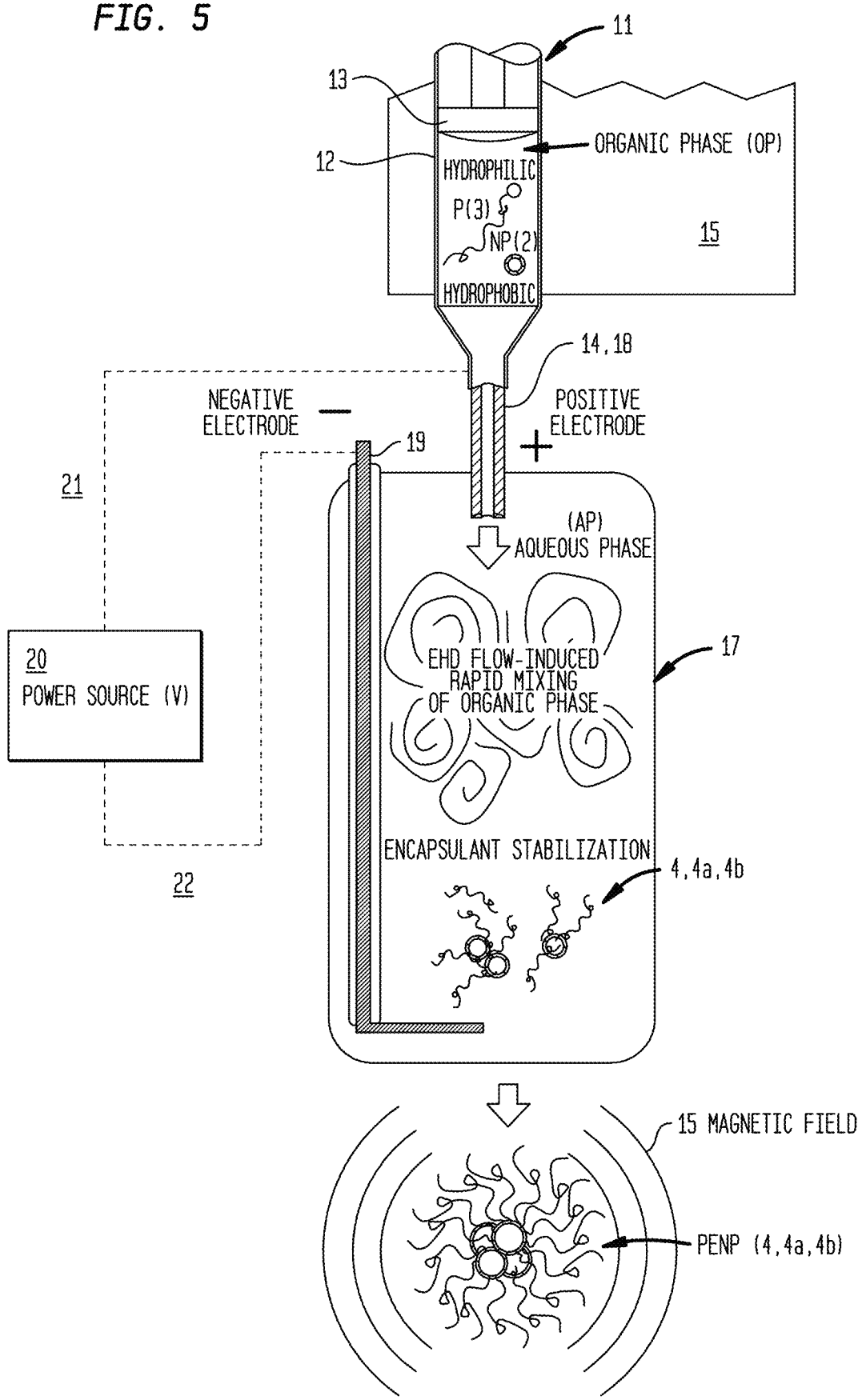

FIG. 5 is block diagram illustrating a method of assembling the polymer encapsulated nanoparticles shown in FIGS. 4A and 4B by use of electrohydrodynamic mixing mediated-nanoprecipitation.

Figure 6B:
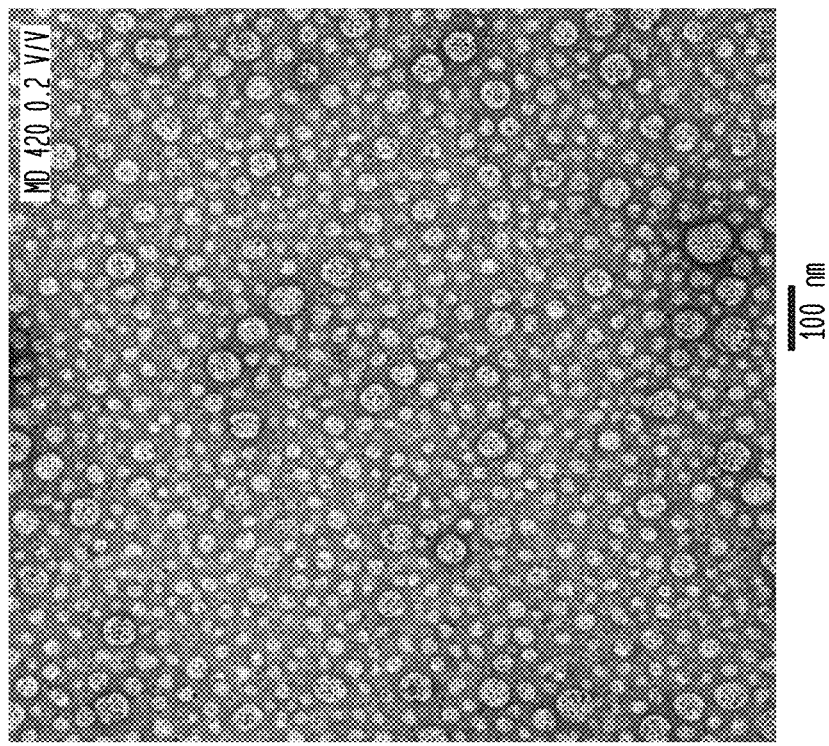
Figure 6A:
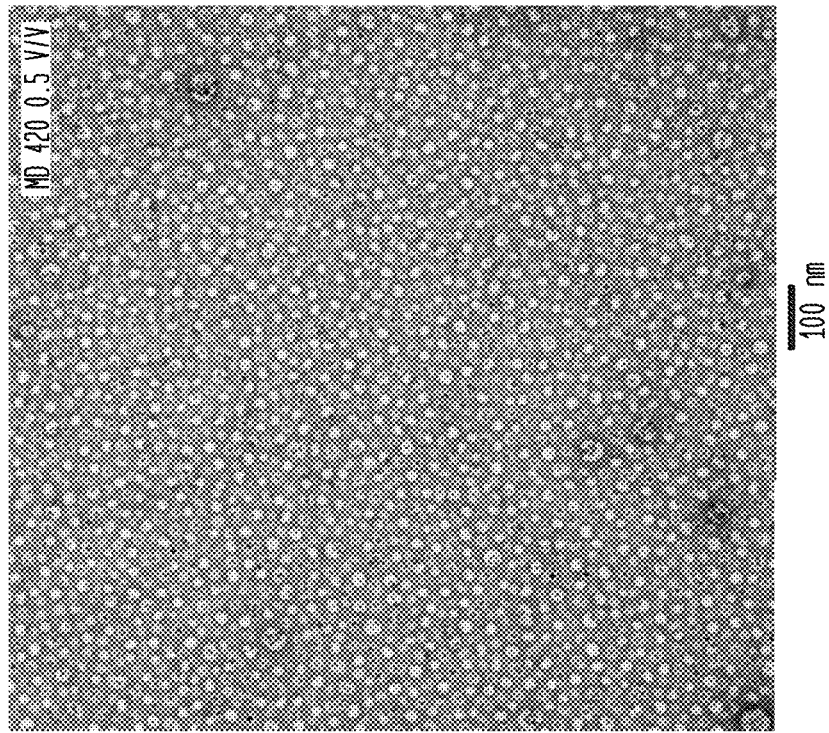

FIG. 6A is a micrograph obtained by transmission electron microscopy of a polymer encapsulated nanoparticle encompassed by FIG. 1, Block 1B including one or more QD encapsulated in a polymer obtained by the polymer synthesis process shown in FIG. 2, Blocks 2A through 2I by use of electrohydrodynamic mixing mediated-nanoprecipitation as illustrated in FIG. 5 using 0.5 v/v of QD in the organic phase.

FIG. 6B is micrograph obtained by transmission electron microscopy of a polymer encapsulated nanoparticle encompassed by FIG. 1, Block 1B including one or more QD encapsulated in a polymer obtained by the polymer synthesis process shown in FIG. 2, Blocks 2A through 2I by use of electrohydrodynamic mixing mediated-nanoprecipitation as illustrated in FIG. 5 using 0.2 v/v of QD in organic phase.

Figure 7B:
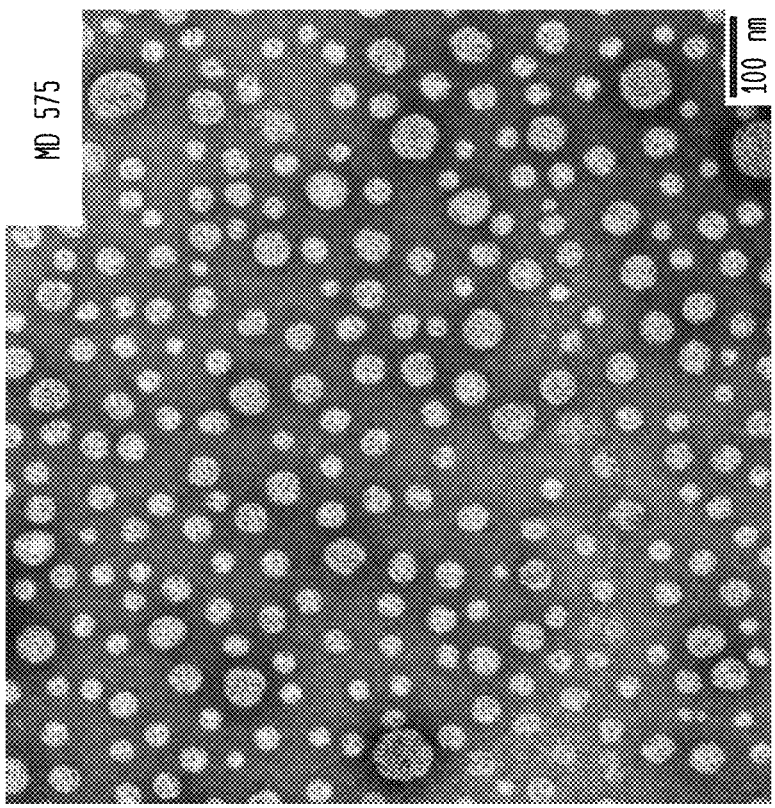
Figure 7A:
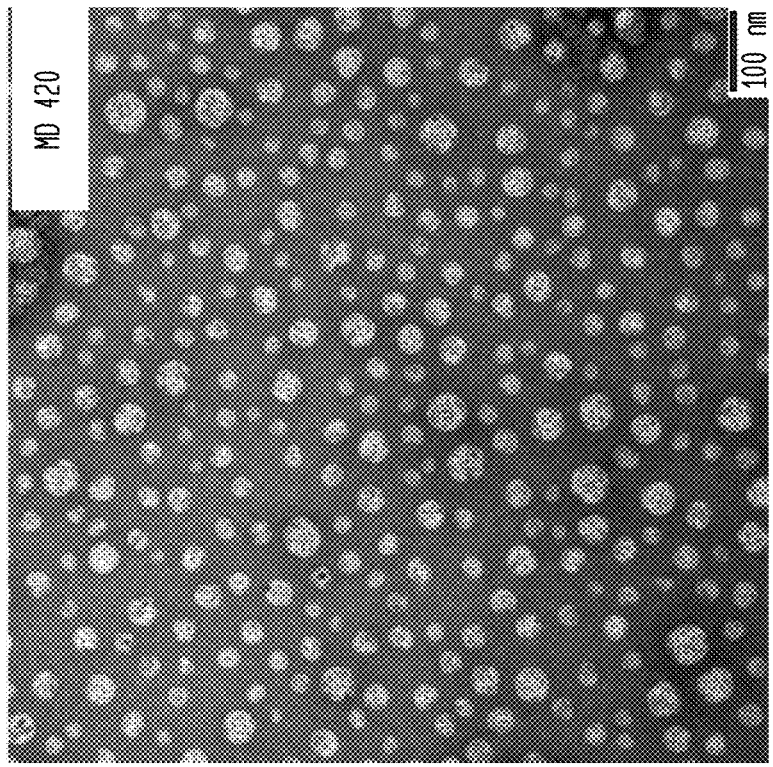

FIG. 7A is micrograph obtained by transmission electron microscopy of a polymer encapsulated nanoparticle encompassed by FIG. 1, Block 1B including one or more QD having an emission wavelength of 420 nm encapsulated in a polymer obtained by the polymer synthesis process shown in FIG. 2, Blocks 2A through 2I by use of electrohydrodynamic mixing mediated-nanoprecipitation as illustrated in FIG. 5.

FIG. 7B is micrograph obtained by transmission electron microscopy of a polymer encapsulated nanoparticle encompassed by FIG. 1, Block 1B including one or more QD having an emission wavelength of 575 nm encapsulated in a polymer obtained by the polymer synthesis process shown in FIG. 2, Blocks 2A through 2I by use of electrohydrodynamic mixing mediated-nanoprecipitation as illustrated in FIG. 5.

Figure 7C:
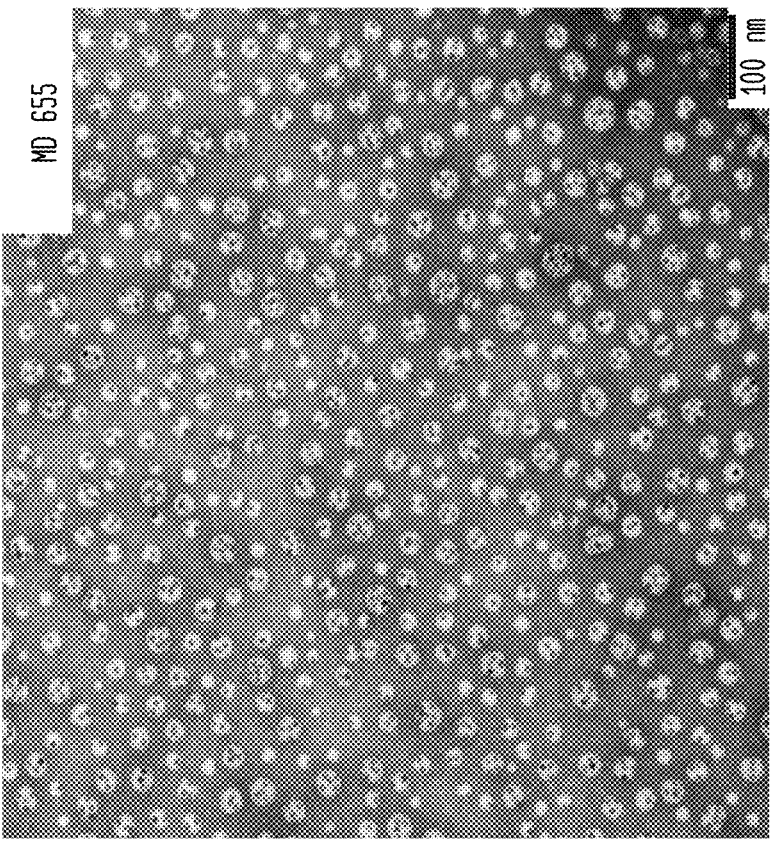

FIG. 7C is micrograph obtained by transmission electron microscopy of a polymer encapsulated nanoparticle encompassed by FIG. 1, Block 1B including one or more QD having an emission wavelength of 610 nm encapsulated in a polymer obtained by the polymer synthesis process shown in FIG. 2, Blocks 2A through 2I by use of electrohydrodynamic mixing mediated-nanoprecipitation as illustrated in FIG. 5.

Figure 7D:
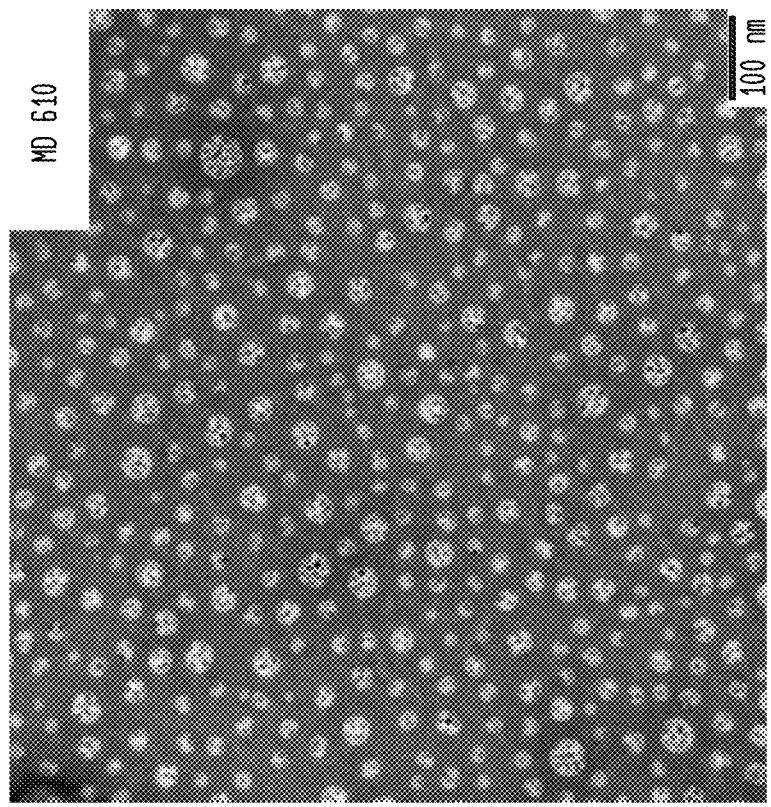

FIG. 7D is micrograph obtained by transmission electron microscopy of a polymer encapsulated nanoparticle encompassed by FIG. 1, Block 1B including one or more QD having an emission wavelength of 655 nm encapsulated in a polymer obtained by the polymer synthesis process shown in FIG. 2, Blocks 2A through 2I by use of electrohydrodynamic mixing mediated-nanoprecipitation as illustrated in FIG. 5.

FIG. 8A is micrograph obtained by transmission electron microscopy of a polymer encapsulated nanoparticle encompassed by FIG. 1, Block 1B including one or more 20 nm SPION and one or more QD having an emission wavelength occurring at 610 nm encapsulated in a polymer obtained by the polymer synthesis process shown in FIG. 2, Blocks 2A through 2I by use of electrohydrodynamic mixing mediated-nanoprecipitation as illustrated in FIG. 5.

FIG. 8B is micrograph obtained by transmission electron microscopy of a polymer encapsulated nanoparticle encompassed by FIG. 1, Block 1B including one or more 15 nm SPION and one or more QD having an emission wavelength occurring at 610 nm encapsulated in a polymer obtained by the polymer synthesis process shown in FIG. 2, Blocks 2A through 2I by use of electrohydrodynamic mixing mediated-nanoprecipitation as illustrated in FIG. 5.

FIG. 8C is micrograph obtained by transmission electron microscopy of a polymer encapsulated nanoparticle encompassed by FIG. 1, Block 1B including one or more 5 nm SPION and one or more QD having an emission wavelength occurring at 610 nm encapsulated in a polymer obtained by the polymer synthesis process shown in FIG. 2, Blocks 2A through 2I by use of electrohydrodynamic mixing mediated-nanoprecipitation as illustrated in FIG. 5.

Figure 9A:
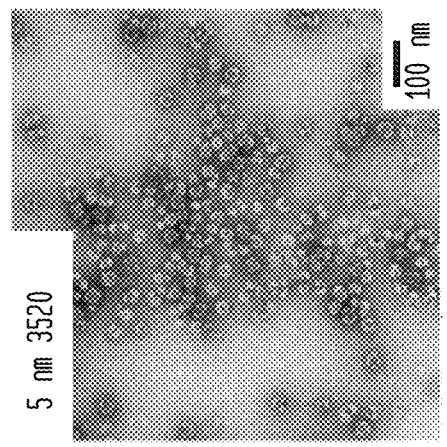

FIG. 9A is micrograph obtained by transmission electron microscopy of a polymer encapsulated nanoparticle encompassed by FIG. 1, Block 1B including a ratio of QD:15 nm SPION:polymer (5:5:20) obtained by the polymer synthesis process shown in FIG. 2, Blocks 2A through 2I and by use of electrohydrodynamic mixing mediated-nanoprecipitation as illustrated in FIG. 5.

Figure 9B:
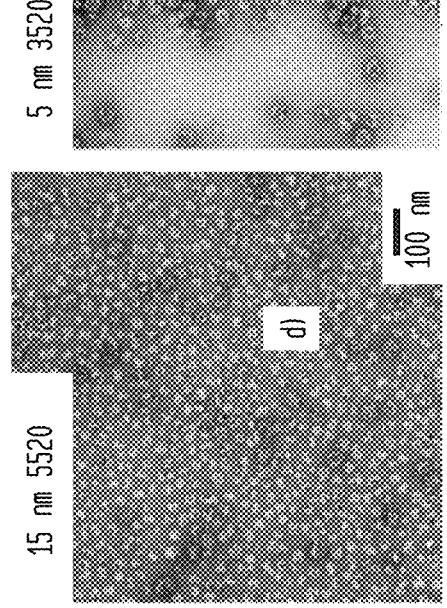

FIG. 9B is micrograph obtained by transmission electron microscopy of a polymer encapsulated nanoparticle encompassed by FIG. 1, Block 1B including a ratio of QD:5 nm SPION:polymer (3:5:20) obtained by the polymer synthesis process shown in FIG. 2, Blocks 2A through 2I and by use of electrohydrodynamic mixing mediated-nanoprecipitation as illustrated in FIG. 5 and having a hydrodynamic diameter of 210±30 nm.

Figure 9E:
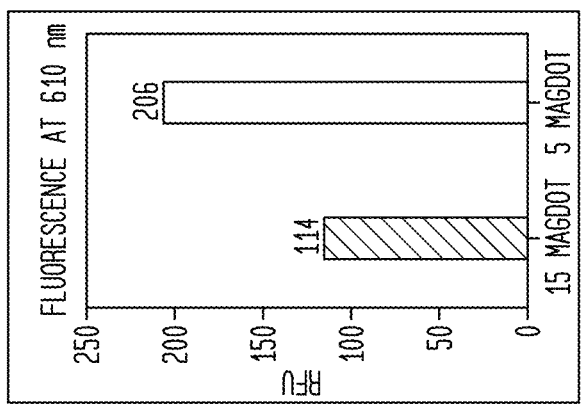
Figure 9D:
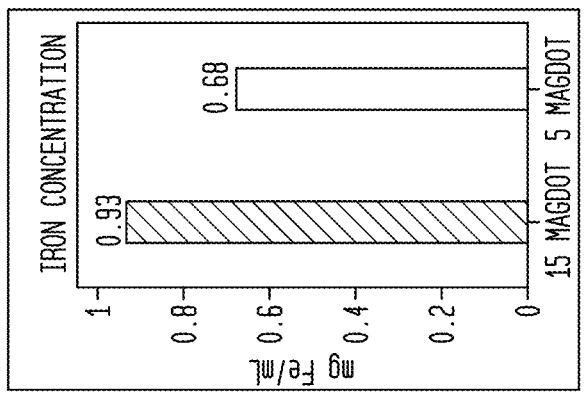
Figure 9C:
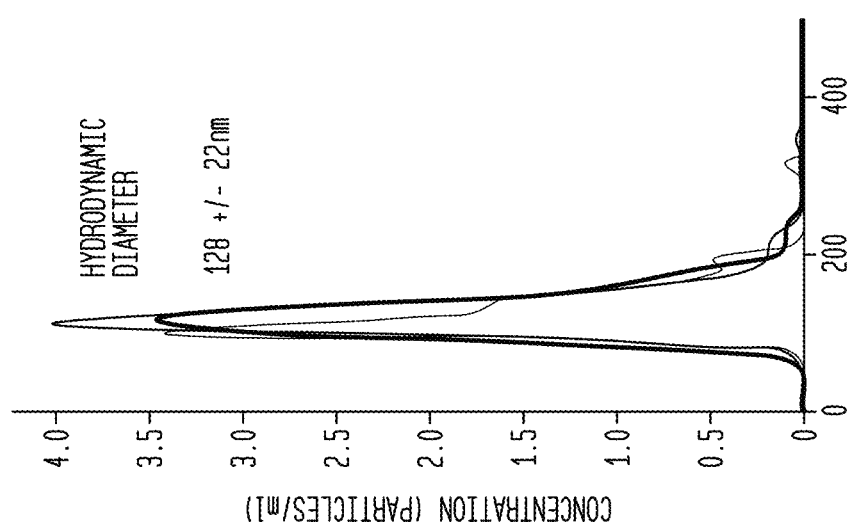

FIG. 9C is a plot of hydrodynamic diameter against concentration of particles per milliliter of the polymer encapsulated nanoparticles shown in FIG. 9A evidencing a hydrodynamic diameter of about 128 nm±22 nm.

FIG. 9D is a bar graph comparing the iron concentration of polymer encapsulated nanoparticle including SPION of 15 nm and QD having an emission wavelength occurring at 610 nm to polymer encapsulated nanoparticle including SPION of 5 nm and QD having an emission wavelength occurring at 610 nm.

FIG. 9E is a bar graph comparing the fluorescence of polymer encapsulated nanoparticle including SPION of 15 nm to polymer encapsulated nanoparticle including SPION of 5 nm.

Figure 10B:
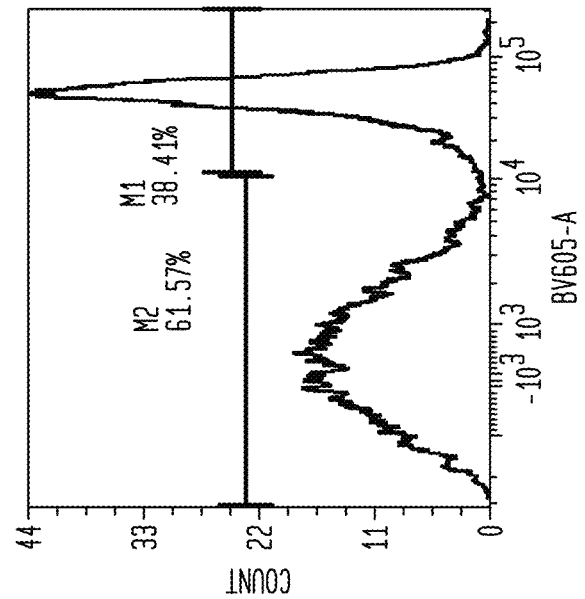
Figure 10A:
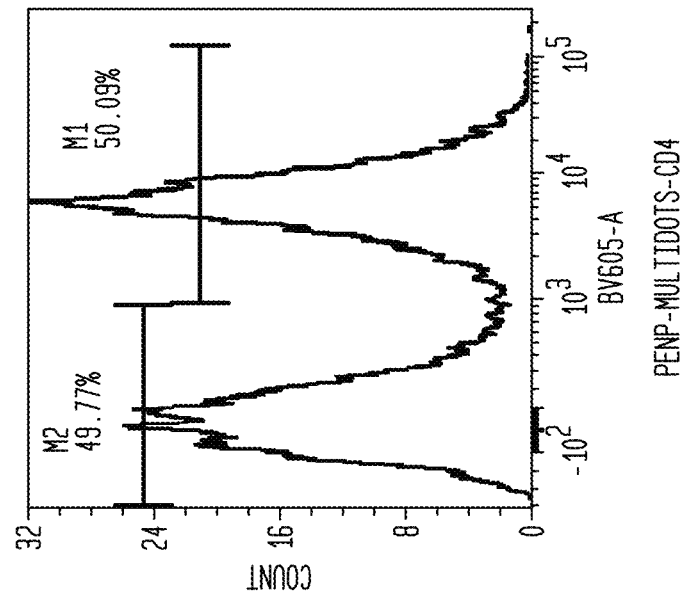

FIG. 10A is a flow cytometry univariant histogram depicting detection of peripheral blood mononuclear cells bound to mouse anti human CD4 linked to a polymer encapsulated nanoparticle encompassed by FIG. 1, Block 1D including one or more QD.

FIG. 10B is a flow cytometry univariant histogram depicting detection of peripheral blood mononuclear cells bound to mouse anti human CD3 linked to a polymer encapsulated nanoparticle encompassed by FIG. 1, Block 1D including one or more QD.

Figure 11C:
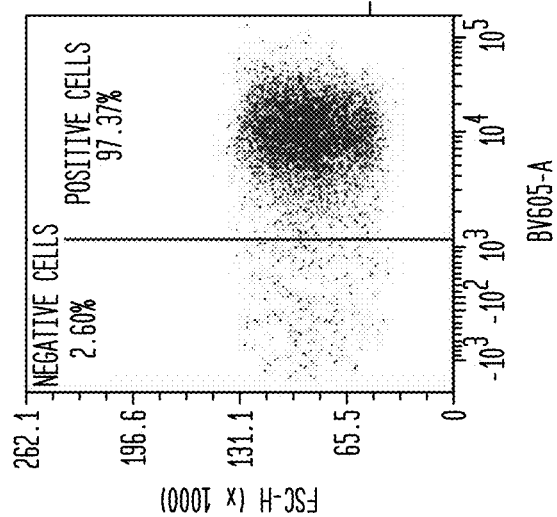
Figure 11B:
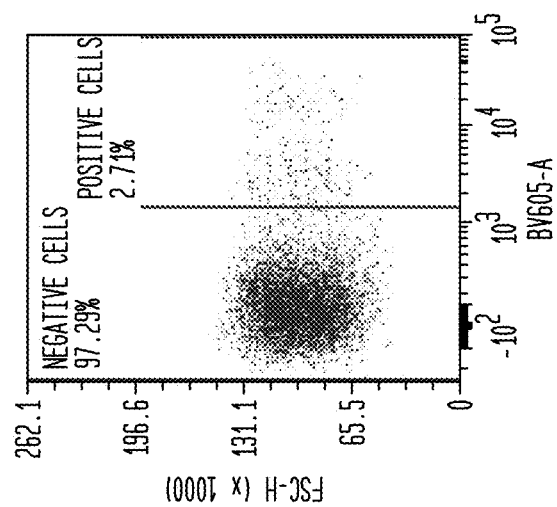
Figure 11A:
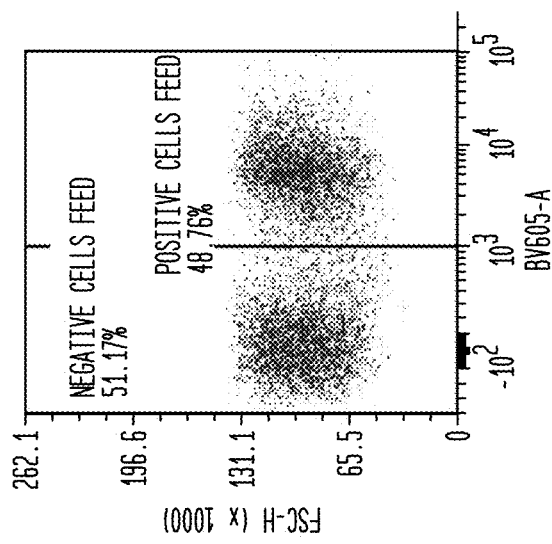

FIG. 11A is flow cytometry bivariant dot plot depicting detection of CD3 positive peripheral blood mononuclear cells bound to mouse anti human CD3 linked to a polymer encapsulated nanoparticle encompassed by FIG. 1, Block 1D including one or more SPION and one or more QD and CD3 negative cells in a reaction solution prior to magnetic separation.

FIG. 11B is flow cytometry bivariant dot plot depicting detection of depleted CD3 positive peripheral blood mononuclear cells in the non-magnetic fraction of the reaction solution subsequent to magnetic separation.

FIG. 11C is flow cytometry bivariant dot plot depicting detection of the enriched CD3 positive peripheral blood mononuclear cells bound to mouse anti human CD3 linked to a polymer encapsulated nanoparticle encompassed by FIG. 1, Block 1D including one or more SPION and one or more QD in the magnetic fraction of the reaction solution subsequent to magnetic separation.

FIG. 12A is a brightfield image of host squid hemocytes incubated with inventive nanocomposites including one or more SPION and one or more QD having an emission wavelength occurring at 610 nm.

FIG. 12B is an epifluorescence image of host squid hemocytes incubated with inventive nanocomposites including one or more SPION and one or more QD having an emission wavelength occurring at 610 nm emission detected by fluorescence microscopy in the fluorescein isothiocyanate ("FITC") channel.

FIG. 12C is composite image of the brightfield and epifluorescence image of host squid hemocytes incubated with inventive nanocomposites including one or more SPION and one or more QD having emission wavelength at 610 nm as detected by brightfield and fluorescence microscopy measured in the FITC channel.

V. DETAILED DESCRIPTION OF THE INVENTION

The present invention may be understood by reference to the following detailed description of aspects of the invention and the examples included therein and to the figures and their previous and following description. Compounds, compositions, articles, devices, or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular embodiments for the purpose of enabling a person of ordinary skill in the art to make and use a numerous and wide variety of embodiments of the invention, even if not explicitly disclosed. Unless defined otherwise, all technical and scientific terms used herein have the same meaning as commonly understood by one of ordinary skill in the art to which this invention belongs. Although any methods and materials similar or equivalent to those described herein can be used in the practice of the present invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein may be different from the actual publication dates, which may need to be independently confirmed.

As used in the specification and the appended claims, the singular forms "a," "an" and "the" include plural referents unless the context clearly dictates otherwise. Thus, for example, reference to "a component," "a polymer," or "a particle" includes mixtures of two or more such components, polymers, or particles, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, as illustrative examples, an ethylene glycol residue in a polyester refers to one or more —OCH$_2$CH$_2$— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

Disclosed are the components to be used to prepare the compositions of the invention as well as the compositions themselves to be used within the methods disclosed herein. These and other materials are disclosed herein, and it is understood that when combinations, subsets, interactions, and groups of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, elements in methods of making and using the compositions of the invention. Thus, if there are a variety of additional elements that can be performed it is understood that each of these additional elements can be performed with any specific embodiment or combination of embodiments of the methods of the invention. It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Process Overview

Now, with primary reference to FIG. 1, a block flow diagram provides a general overview of the nanomaterial polymer encapsulation system (1) including one or more of: polymer synthesis (Block 1A) of a nanoparticle ("NP") (2) encapsulation polymer ("P") (3); formation of polymer encapsulated nanoparticles ("PENP") (4) (Block 1B); preparation of antibodies, half-antibodies, antibody fragments (individually or collectively "Ab") (5) (Block 1C); preparation of PENP antibody conjugates ("PENP-Ab") (6) (Block 1D); PENP-Ab cell labeling ("PENP-Ab-Cells") (7), flow cytometry analysis (8) and imaging of PENP-Ab-Cells (7) (Block 1E).

Polymer Synthesis.

Now, with primary reference to FIG. 2, a block flow diagram provides an overview of an illustrative polymer synthesis process of FIG. 1, Block 1A. Referring to Block 2A of the process, aminopolystyrene ("PS-NH$_2$") having linear formula $(C_8H_8)_nCH_5N$, wherein the PS molecular weight can occur in a range of about 1.5 kDa to about 40 kDa, can be obtained from Polymer Source, Inc., PN P3965-SNH$_2$, comprising Formula I. Particular embodiments can include PS-NH$_2$ having a number averaged molecular weight of about 9.5 kDa.

Formula I

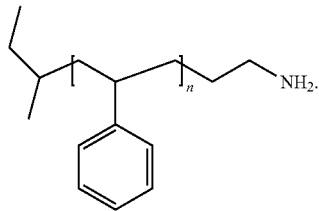

Now, referring to FIG. 2, Block 2B of the polymer synthesis process, dibenzocylooctyne-N-hydroxysuccinimidyl ester ("DBCO-NHS Ester") having liner formula $C_{23}H_{18}N_2O_5$ (CAS No.: 1353016-71-3) and having a molecular weight of 402.40 g/mol can be obtained from Click Chemistry Tools, PN A133-100 comprising Formula II.

Formula II

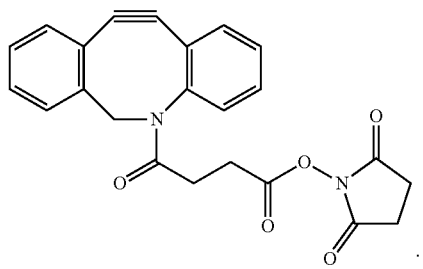

Now, referring to FIG. 2, Block 2C of the polymer synthesis process, PS-NH$_2$ can be reacted with DBCO-NHS Ester to produce polystyrene-dibenzocylooctyne ("PS-DBCO") comprising Formula III.

Formula III

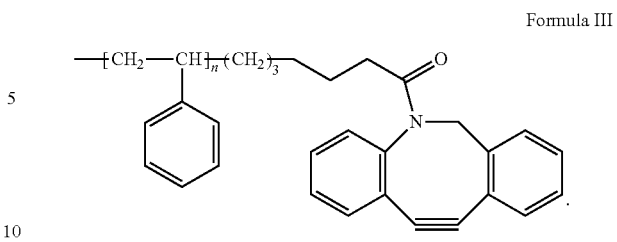

An example of a scalable procedure for the production of PS-DBCO can include thawing PS-NH$_2$ 20 mg for 15 minutes at room temperature ("RT") and thawing DBCO-NHS-Ester 10 mg for 15 minutes ("min.") at RT. Aliquot 1 mL of toluene ($C_6H_5CH_3$) (CAS No.: 108-88-3) to the PS-NH$_2$ 20 mg and vortex for 15 minutes at 500 RPM. Centrifuge DBCO at 1500 relative centrifugal force ("RCF") (RCF=(RPM)$^2$×1.118×10$^{-5}$×r) for 30 seconds ("sec.") at about 25° C. (about 77° F.). Aliquot 1 mL of toluene to the DBCO. Sonicate the DBCO for 5 min. in RT water. Transfer 1 mL of DBCO in toluene to PS-NH$_2$ in toluene. Vortex DBCO in PS-NH$_2$ mixture for 16 to 24 hours ("hr.") at 500 RPM at RT.

Now, referring to FIG. 2, Block 2D of the polymer synthesis process, an 8-arm polyethylene glycol-amine ("PEG$_{8-arm}$-NH$_2$") comprising a multi-arm PEG derivative with amine groups at each terminal of the eight arms connected to one hexaglycerol core having linear formula R(O(CH$_2$CH$_2$O)nCH$_2$CH$_2$NH$_2$)$_8$ and a number averaged molecular weight of about 19.5 kDa can be obtained from Nanosoft Polymers, PN 2443, comprising Formula IV and further shown in Formula V.

Formula IV

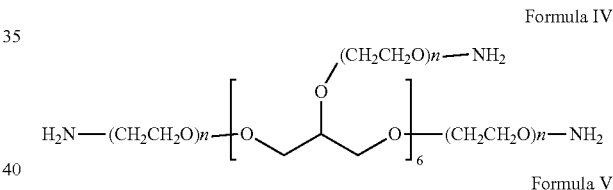

Formula V

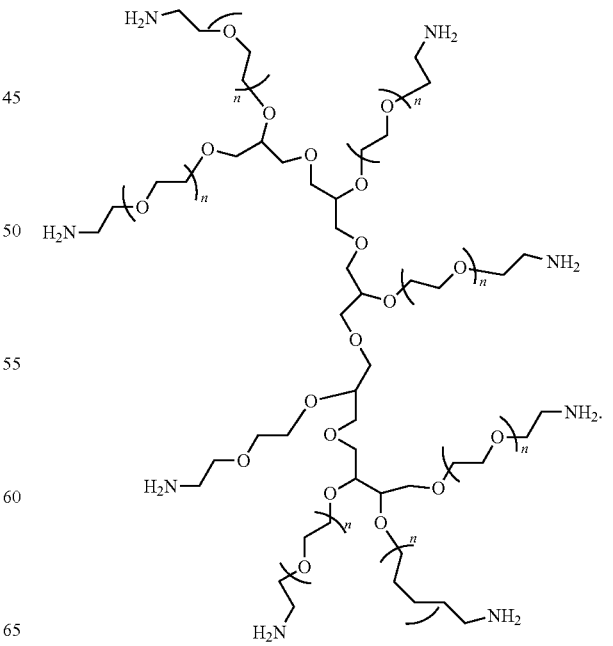

In particular embodiments, a 4-arm polyethylene glycol-amine, a 6-arm polyethylene glycol-amine, or an 8-armpolyethyleneglycol-amine, or combinations thereof, can also be utilized having corresponding PEG molecular weights of 10 kDa, 20 kDa, or 40 kDa.

Now, referring to FIG. 2, Block 2E of the polymer synthesis process, an azido-d-polyethylene glycol 4-N-hydroxysuccinimidyl ester ("Azido-PEG$_4$-NHS Ester") having a molecular weight of 388.37 g/mol (CAS No.: 944251-24-5) can be obtained from Click Chemistry tools PN AZ103-100 comprising Formula VI.

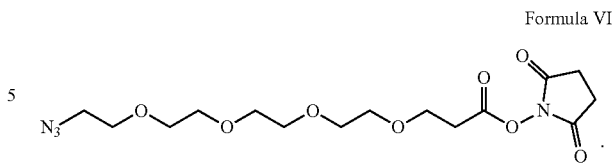

Formula VI

Now, referring to FIG. 2, Block 2F of the polymer synthesis process, PEG$_{8arm}$-NH$_2$ can be reacted with Azido-PEG$_4$-NHS Ester to produce branched polyethylene glycol ("PEG-Amine-Azide") comprising Formula VII.

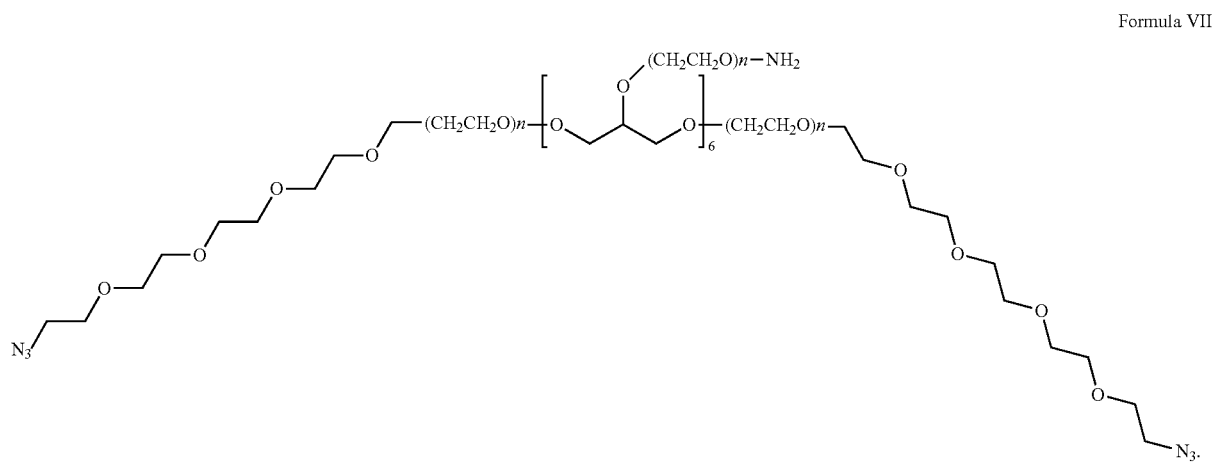

Formula VII

An example of a scalable protocol for the production of PEG-Amine-Azide can include thawing 40 mg of PEG$_{8\text{-}arm}$-NH$_2$ for 15 min. at RT and thawing 80 μl of Azido-PEG$_4$-NHS Ester (50 mM) for 15 min. at RT. Aliquot 400 μl of methanol (CAS NO.: 6756-1) to PEG$_{8\text{-}arm}$-NH$_2$ and vortex the PEG$_{8\text{-}ram}$-NH$_2$ for 15 min. at 500 RPM. Centrifuge Azido-PEG$_4$-NHS at 1500 RCF for 30 sec. at 25° C. (about 77° F.). Transfer the Azido-PEG$_4$-NHS 80 μl to the 400 μl of PEG$_{8\text{-}arm}$-NH$_2$. Vortex for 16 to 24 hr. at 500 RPM at RT.

Now, referring to FIG. 2, Block 2G of the polymer synthesis process, PS-DBCO obtained in Block 2C of the synthesis process can be purified by the following illustrative scalable procedure including transferring 400 μl of PS-DBCO to each of five centrifuge tubes. Aliquot 800 μl of methanol to each of the five centrifuge tubes. Mix PS-DBCO in methanol by inversion of each of the five centrifuge tubes. Centrifuge the PS-DBCO in methanol for 5 min. at 20,000 RCF at 15° C. to 25° C. (about 59° F. to about 77° F.). Decant the supernatant from each of five centrifuge tubes. Add 400 μl of toluene to each of the five centrifuge tubes. Place the five centrifuge tubes in a water bath at 37° C. (about 98.6° F.) for 2 min. Dissolve the PS-DBCO pellet in 400 μl toluene by mixing with a pipette. Add 800 μl of methanol to each of the five centrifuge tubes. Invert each centrifuge tube to mix contents. Centrifuge at 20,000 RCF for 5 min. at 15° to 25° C. (about 59° F. to about 77° F.). Decant the supernatant from each of five centrifuge tubes. Add 400 μl of toluene to each of the five centrifuge tubes. Place the five centrifuge tubes in a water bath at 37° C. (about 98.6° F.) for 2 min. Dissolve the PS-DBCO pellet in toluene by mixing with a pipette.

Now, referring to FIG. 2, Block 2H of the polymer synthesis process, PS-DBCO obtained in Block 2G of the synthesis process can be reacted with PEG-Amine-Azide obtained in Block 2F of the polymer synthesis process to produce polystyrene-b-poly (ethylene glycol) amine ("PS-b-PEG-NH$_2$") comprising Formula VIII.

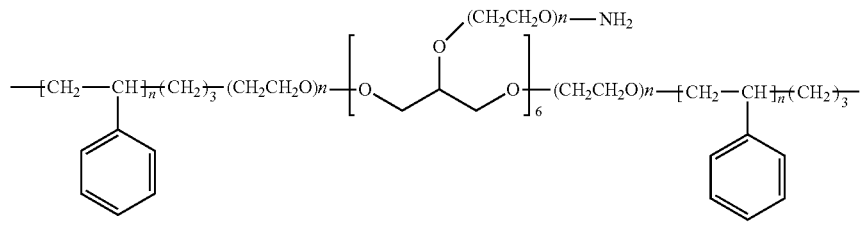

Formula VIII

In the instant illustrative example of Block 2H, the PS-DBCO in toluene of all five centrifuge tubes from Block 2G and PEG-Amine-Azide in methanol obtained in Block 2F can be transferred to a 4 mL glass vial. Vortex the mixture of PS-DBCO and PEG-Amine-Azide at 500 RPM at RT for 16 to 24 hr. to produce PS-b-PEG-$NH_2$ comprising Formula VIII. The PS-b-PEG-$NH_2$ can comprise PS having molecular weights ranging from about 1.5 kDa to about 40 kDa and can comprise PEG having molecular weights ranging from about 10 kDa to about 40 kDa.

Referring to FIG. 2, Block 2I of the synthesis process, the PS-b-PEG-$NH_2$ obtained in Block 2H can be purified and dried by the following illustrative scalable procedure including cooling hexane (CAS No.: 110-54-3) at −20° C. (about −4° F.) for 15 min. Aliquot approximately 1.25 mL of PS-b-PEG-$NH_2$ obtained in Block 2I of the synthesis process into a 15 mL centrifuge tube. Slowly add 12 mL of hexane to the centrifuge tube containing PS-b-PEG-$NH_2$. Mix the PS-b-PEG-$NH_2$ in toluene/hexane by gently tilting the centrifuge tube 10 to 15 times. Place the centrifuge tube at −20° C. (about −4° F.) for 5 min. to cool the PS-b-PEG-$NH_2$ in toluene/hexane. Decant the supernatant from the PS-b-PEG-$NH_2$ pellet. Aliquot 1 mL of tetrahydrofuran to the centrifuge tube. Place the centrifuge tube in a water bath at the 37° C. (about 98.6° F.) for 2 min. Dissolve the PS-b-PEG-$NH_2$ pellet by mixing with a pipette. Slowly add 6 mL of cold hexane to the centrifuge tube. Gently tilt the centrifuge tube 10 to 15 times until PS-b-PEG-$NH_2$ precipitates as flakes are visualized with clear supernatant. Place the centrifuge tube at −20° C. (about −4° F.) for 5 min. Decant the supernatant from the PS-b-PEG-$NH_2$ pellet. Place the centrifuge tube containing the PS-b-PEG-$NH_2$ pellet at RT for 24 hr. to remove excess solvents and to obtain a dry PS-b-PEG-$NH_2$. Store at −20° C. (about −4° F.).

Figure 3:
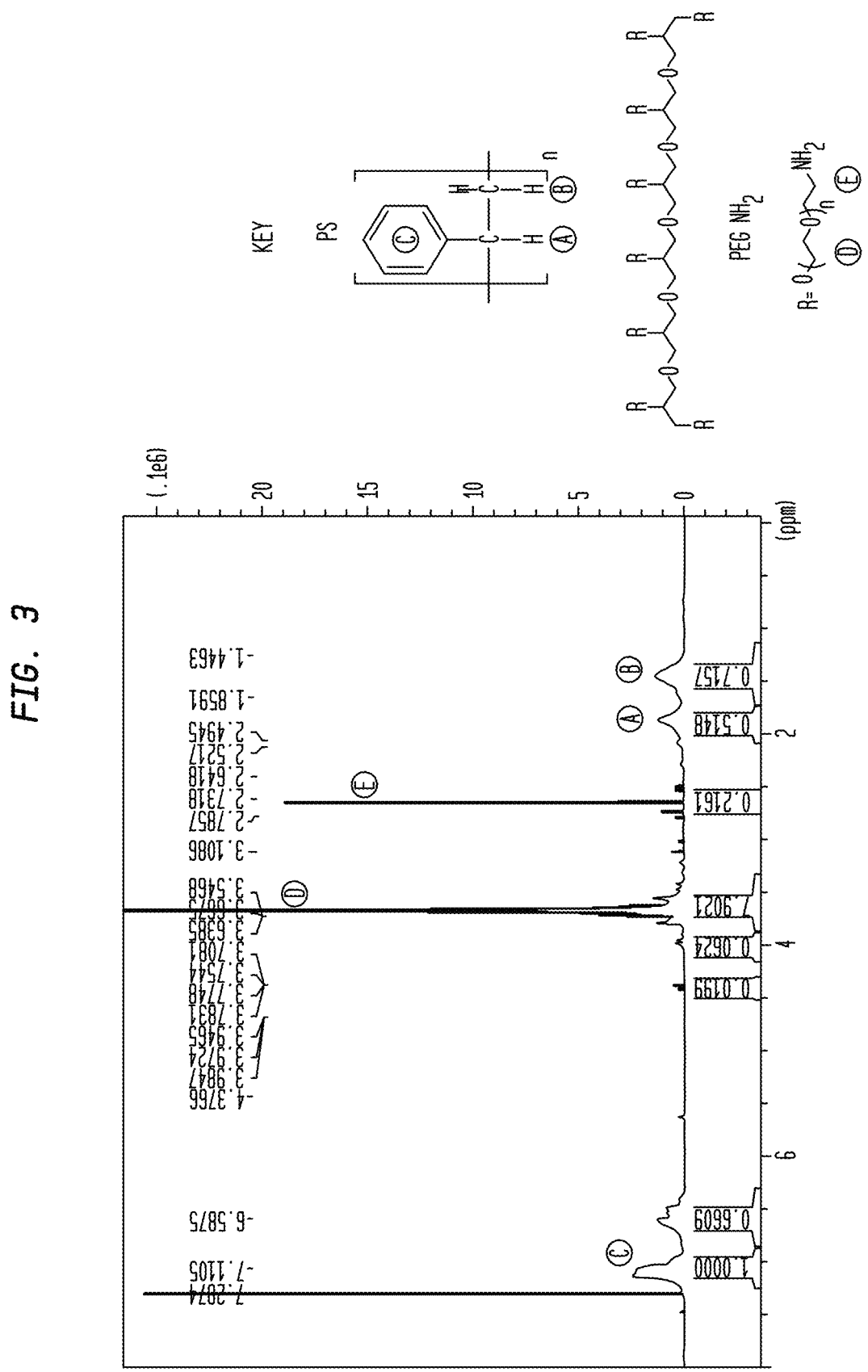
FIG. 3 is an NMR spectrum which validates the molecular structure of the illustrative example of PS-b-PEG-$NH_2$ obtained by the polymer synthesis process shown in FIG. 2, Blocks 2A through 2I.

Now, referring primarily to FIG. 3, the structure of the PS-b-PEG-$NH_2$ obtained in Block 2I of the synthesis process can be analyzed using nuclear magnetic resonance ("NMR"). The NMR spectrum shown in FIG. 3 validates the molecular structure obtained by the polymer synthesis process shown in FIG. 2, Blocks 2A through 2I, and above disclosed polymer synthesis procedure, is purified PS-b-PEG-$NH_2$ comprising formula VIII.

The illustrative example of the polymer PS-b-PEG-$NH_2$ obtained in Block 2I is not intended to preclude embodiments of the PS-b-PEG including functional groups other than $NH_2$. Other functional groups can include as examples, one or more of: acrylate, maleimide, vinylsulfone, azide, biotin, carboxyl, thiol, alkyne, hydrazide, N-hydroxysuccinimide ester, and nitrophenyl carbonate, and combinations thereof, or embodiments including other similar or equivalent polymers including one or more functional groups.

Formation of Polymer Encapsulated Nanoparticles.

Now, with primary reference to FIG. 4A which illustrates a particular embodiment of PENP (4) including one or more QD (2a) encapsulated in a polymer ("P") (3) having a hydrophobic region which can associate or coordinate with the one or more QD (2a) and a hydrophilic region including a functional group (9) which can associate with an aqueous environment, and in particular embodiments, the polymer (P) (3) can comprise PS-b-PEG-$NH_2$ obtained in Block 2I, which by solution based association can produce polymer encapsulated nanoparticles including one or more QD (2a) ("PENP-MultiDots") (4a).

Now, with primary reference to FIG. 4B, which illustrates a particular embodiment of PENP (4) including one or more QD (2a) and one or more SPION (2b) encapsulated in a polymer ("P") (3) having a hydrophobic region which can associate or coordinate with the one or more SPION (2b) and optionally one or more QD (2a) and a hydrophilic region including a functional group (9) which can associate with an aqueous environment, and in particular embodiments, the polymer (P) (3) can comprise PS-b-PEG-$NH_2$ obtained in Block 2I, which by solution based association can produce PENP (4) including one or more SPION (2b) and one or more QD (2a) ("PENP-MagDots") (4b).

Now, with primary reference to FIG. 4C, a numerous and wide variety of agents (5) can be conjugated to PENP-MultiDots (4a) and/or PENP-MagDots (4b) using the functional group (9) of the polymer (3), and in particular embodiments, the amine afforded by PS-b-PEG-$NH_2$. The example of PENP-MagDots (4b) in FIG. 4C illustrates that one or more agents (5) can be conjugated to PENP-MultiDots (4a) and/or PENP-MagDots (4b) by activating the functional group (9), including as illustrative examples: one or more linkers (10, 10a, 10b), a polyethylene glycol, a fluorescent probe, an aptamer, a vitamin, a radioactive isotope, a contrast media, a surface charge modifier, a lectin, a protein, a peptide, a cell surface receptor, a cell coat, and combinations thereof. Specifically, in particular embodiments the functional group (9) can be utilized to directly or indirectly through one or more linkers (10, 10a, 10b) couple an antibody or antibody fragment (Ab) (5') to produce PENP antibody conjugates (6) including as illustrative examples PENP-MultiDots-Ab (6a) and PENP-MultiDots-Ab (6b).

Now, with primary reference to FIG. 5, scalable, solution-based production of PENP (4) encompassed by the invention, including, but not necessarily limited to, PENP-MagDots (4b) or PENP-MultiDots (4a), can be prepared by conventional self-assembly, flash nanoprecipitation (FNP) comprising rapid turbulent mixing generated by high velocity flows, as described by Yanjie Zhang, a Aaron R. Clapp, *RSC Advances*, Issue 89, 2014 "Preparation of quantum dot-embedded polymeric nanoparticles using flash nanoprecipitation", or by rapid mixing induced by electrohydrodynamics ("EHD"): EHD mixing mediated-nanoprecipitation ("EHD-NP"). Kil Ho Lee, Guolingzi Yang, Barbara E. Wyslouzil and Jessica O. Winter, *ACS Appl. Polym. Mater.* 2019, 1, 4, 691-700, each incorporated by reference herein.

The illustrative EHD mixing system of FIG. 5 can include a syringe (11) having a syringe barrel (12) fitted with a sliding syringe plunger (13), and a syringe needle (14). A syringe pump (15) configured drive the syringe plunger (13) to deliver an organic phase of water-miscible nonpolar aprotic solvents ("OP") including solubilized (P) (3) and NP (4) whether QD (2a) and/or SPIONS (2b) (collectively the "inorganics") at a predetermine volumetric flow rate into an aqueous phase ("AP"). The illustrative example of a syringe (11) and a syringe driver (15) is not intended to preclude other appliances useful in delivering the OP into the AP at a predetermined volumetric flow. The concentration of inorganics per unit volume of the OP can be about 0.1 volume to volume ("v/v") to about 0.5 v/v. The concentration of P (3) to QD (2a) and/or SPION (2b) in the OP by mass can be about 1:1 to about 4:1. The amount of P (3) can be adjusted to obtain a PENP (4) having a substantially uniform hydrodynamic diameter ("HD") that occurs in size range of about 40 nanometers ("nm") to about 500 nm. In embodiments in which the QD (2a) and/or the SPIONS (2b) are passivated with a ligand (16), the ligand mass relative to the total inorganics mass can be about 20% to 40% by mass. A ligand mass percent greater than 40% can interfere with the assembly of the PENP (4).

A non-electrically conductive container (17) can hold the AP, typically distilled or deionized water. A positive electrode (18) and a negative electrode (19) can be introduced about 1 cm apart in the AP held by the non-electrically conductive container (17). In particular embodiments the syringe needle (14) can, if electrically conductive, act as the positive electrode (18). A voltage source (20) can supply a voltage ("V") to the positive terminal (18) to generate an electrical field between the positive electrode (18) and negative electrode (19) in the AP. The syringe plunger (13) can be driven to introduce the OP into the AP at a consistent flow rate of about 8 mL $h^{-1}$ to about 15 mL $h^{-1}$. Voltage (V) can be adjusted between about −1 kilovolt ("kV") and about −2.5 kV. The electric field can generate a fine dispersion of OP in the AP to produce PENP (4), PENP-MagDots (4b), or PENP-MultiDots (4a) of substantially uniform size. The resulting size of the PENP (4), PENP-MagDots (4b), or PENP-MultiDots (4a) can increase with increasing V and/or concentration of inorganics per unit volume of the OP. The resulting PENP-MagDots (4b) can be subsequently isolated by influence of a magnetic field (15).

PENP-MultiDots.

PENP-MultiDots (4a) can include QD (2a) inorganic semiconductor nanocrystals comprising an inorganic core semiconductor material (2a') (also referred to as a "core material") surrounded a shell semiconductor material (2a") (also referred to as a "shell material") having a different band gap (annotated as "core material/shell material") (e.g. CdS/ZnS). QD (2a) can have a size that typically occurs in the range of 1 nm to 10 nm. QD (2a) can exhibit size-variable emission color due to the quantum confinement effect, where smaller QD (2a) emit at higher energy (lower wavelength) and larger QD (2a) emit at lower energy (higher wavelength) for a given composition. Accordingly, QD (2a) can absorb over a broad range and have photoluminescence emission over a narrow range which can be tuned depending on the material from which the QD (2a) is made and the size of the QD (2a). Illustrative examples of QD core/shell compositions, and combinations thereof, suitable for use in embodiments of the PENP-MultiDots (4a) can include one or more of: CdS/ZnS, CdSSe/ZnS, CdSe/ZnS, CdTe/ZnS, and CdSeTe/ZnS each having an emission photoluminescence occurring in the range of 420 nm to 880 nm; CuInZnS/ZnS, 540 to 660 nm; and PbS/CdS, 700 nm to 900 nm. However, these examples are not intended to preclude embodiments having other QD (2a) core/shell compositions.

Purified QD (2a) can be bare or can be capped to control QD particle size and/or to prevent QD agglomeration. QD (2a) synthesized by prototypical hot-injection method can be capped with a ligand (16), such as, oleylamine and oleic acid after QD purification. $^1$H NMR spectroscopy analysis evidence that ligand binding can be highly dynamic, and that oleylamine selectively binds to the surface as oleylammonium bromide in an $NC(X)_2$ binding motif. Only in the presence of excess oleylamine added after purification does oleic acid bind to the surface, in the form of oleylammonium oleate. Protesescu L, Yakunin S, Bodnarchuk M I, Krieg F, Caputo R, Hendon C H, Yang R X, Walsh A, Kovalenko M V, *Nano Lett.* 2015, 15, 3692-3696, hereby incorporated by reference herein. While the use of oleylamine and oleic acid as a capping ligand (16) is suitable for embodiments of the invention, this is not intended to preclude embodiments using other capping ligand(s) (16), as examples, trioctylphosphine oxide, L-histidine, chitosan, polyvinyl alcohol, polyvinylpyrrolidone or combinations thereof.

Typically, bare QD (2a) or capped QD (2a) reach a required level of water solubility and biocompatibility by surrounding the QD (2a) with a P (3) to produce PENP (4). A P (3) suitable for use with embodiments of the invention can include various embodiments of PS-b-PEG-$NH_2$ obtained in Block 2I of the synthesis process, above described. Embodiments of PENP (4) can be produced through the use of various combinations of one or more of: QD (2a), capping ligand (16), and PS-b-PEG-$NH_2$ having PS molecular weights ranging from about 1.5 kDa to about 40 kDa and PEG having molecular weights ranging from about 10 kDa to about 40 kDa.

An illustrative example of a scalable method of production PENP (4), including but not necessarily limited to, PENP-MultiDots (4a), by EHD can include one or more of: constitute PS-b-PEG-$NH_2$ obtained in FIG. 2, Block 2I at 10 mg/mL into a first 1.5 mL tube. Introduce 240 μl of the desired QD at 5 mg/mL (2a) into a second 1.5 mL tube. Transfer 480 μl of acetone/methanol (60/40) to the QD (2a) in the second 1.5 mL tube. Centrifuge the second 1.5 mL tube containing the QD (2a) at 7000 RCF for 1 min. and then remove supernatant with a 200 μL pipette. Transfer 480 μL of anhydrous tetrahydrofuran ("THF") to the second 1.5 mL tube containing the QD and mix thoroughly with a pipette. Introduce into a fresh 1.5 mL centrifuge tube 240 μl of THF, 240 μl QD in THE, and 120 μl of the solubilized PS-b-PEG-$NH_2$ to produce the OP for EHD.

Particular embodiments, EHD can be performed by cleaning the EHD mixing system syringe (11) three times with THE. Load about 0.6 mL of the OP into the syringe barrel (12). Mix the inorganics in the OP thoroughly while loading the syringe (11). Attach the syringe (11) to the syringe pump (15) and set the syringe pump (15) to generate a flow rate of the OP containing the inorganics from the syringe needle (14) in the range of about 11.00 mL/hr. to about 14.00 mL/hr. In particular embodiment the flow rate can be about 12.5 mL/hr. In particular embodiment the flow rate can be about 12.5 mL/hr. Prime the syringe needle (14) until a drop of the OP forms at the end of the syringe needle (14). Twice rinse a 20 mL glass vial (17) with distilled or deionized water (individually or collectively "DI water"). Introduce about 10 mL of DI water into the 20 mL glass vial. Submerge the syringe needle (14) into the 20 mL glass vial (17). Clean the negative electrode (19) by submerging in THF, wipe, and rinse with DI water. Place the negative electrode (19) into the AP contained in the 20 mL glass vial. Place the positive electrode (18) into the AP contained in the 20 mL glass vial (17). In particular embodiments the syringe needle (14), if electrically conductive, can act as the positive electrode (18). Observe that the positive electrode (18), the negative electrode (19), and the syringe needle (14) do not contact. Connect the positive lead (21) from the voltage source (20) to the positive electrode (18) or syringe needle (14) and connect the negative lead (22) from the voltage source (20) to the negative electrode (19). Verify that the voltage source (20) delivers about −1500 V.

The EHD-NP (4) produced by mixing the OP with the AP under influence of the electrical field can be concentrated using centrifugal filtration. The contents of the 20 mL glass vial (17) can be transferred to a 100 kDa cutoff centrifugal ultrafiltration column ("CUC"), as an example, SigmaAldrich PN UFC9010D Amicon® Ultra-15 Centrifugal Filter Unit. Centrifuge the CUC at 3000 RCF for 30 min. at about 25° C. (about 77° F.). Transfer 10 mL 50 mM sodium borate, 100 mM sodium phosphate, 7.3-7.5 pH ("borate buffer") to the CUC. Centrifuge the CUC at 3000 RCF for 30 min. at about 25° C. (about 77° F.). Transfer EHD-NP filtrate from the CUC into a 1.5 mL microcentrifuge tube. Measure and record the volume of the collected EHD-NP filtrate. Transfer 15 μl of EHD-NP filtrate from the 1.5 mL microcentrifuge tube to a 1.5 mL tube and add 285 μl borate buffer. Transfer 290 μl of EHD-NP filtrate to a spectrophotometer cuvette. Measure and record optical density with a spectrophotometer at 450 nm ($OD_{450}$).

The EHD-NP filtrate may contain aggregates of PENP-MultiDots (4a) or aggregates of polymer (P) (3) lacking a QD (2a) (individually and collectively "aggregate"). The aggregate can be substantially removed from the EHD-NP filtrate to produce substantially pure PENP-MultiDots (4a). A scalable method for purification of PENP-MultiDots (4a) can include one or more of: transfer of 120 μl aliquots of the EHD-NP filtrate from the centrifugal ultrafiltration column to corresponding 1.5 mL tubes. Centrifuge the 1.5 mL tubes containing the EHD-NP filtrate at 3,000 RCF for 10 min. to pellet aggregates. Without disturbing the aggregate pellet, remove PENP-MultiDots (4a) containing supernatant. Measure and record the volume of the PENP-MultiDots supernatant. Mix 15 μl of PENP-MultiDots supernatant and 285 μl of borate buffer in 1.5 mL tube. Transfer 290 μl of the mixture to a spectrophotometer cuvette. Measure and record optical density with spectrophotometer at 450 nm ($OD_{450}$).

Now, with primary reference to FIG. 6A and FIG. 6B, the morphology of PENP-MultiDots (4a) produced by the above EHD method at concentration of P (3) and QD (2a) in the OP at 0.5 v/v and 0.2 v/v can be characterized by the use of transmission electron microscopy ("TEM") to produce micrographs of the PENP-MultiDots (4a). PENP produced at concentration of QD (2a) in the OP at 0.5 v/v as shown in the example of FIG. 6A can load fewer QD (2a) per PENP (4) in comparison with PENP (4) produced at concentration of QD (2a) in the OP at 0.2 v/v as shown in the example of FIG. 6B that load more QD (2a) per PENP (4) which evidences that concentration of P (3) and QD (2a) in the OP can be adjusted to affect size and fluorescence per PENP-MultiDot (4a).

Embodiments of PENP-MultiDots (4a) evidence hydrodynamic diameter ("HD") and polydispersity index ("PDI") and size stability suitable for effective clinical and non-clinical applications. Hydrodynamic diameter and PDI can be obtained by performing dynamic light scattering measurements using NanoBrook 90 Plus particle size analyzer. Size histograms can be plotted using SigmaPlot (Systat Software Inc., San Jose, CA, U.S.A.), and size distributions can be fit to log-normal distributions.

HD is defined as the size of a hypothetical hard sphere that diffuses in the same fashion as that of the particle being measured. Though in practice, macromolecules or particles in solution are solvated, dynamic and non-spherical. Due to this, the diameter calculated from the particle's diffusional properties will signify the apparent size of the solvated/dynamic hydrated particle. The HD of the PENP-MultiDots (4A) produced by the above EHD method can vary depending on the parameters used during EHD to produce PENP (4). The TEM micrographs shown in FIG. 6A and FIG. 6B evidence PENP-MultiDots (4a) having substantially consistent HD of about 40 nm to about 50 nm; however, by varying the parameters used during EHD, PENP-MultiDots (4a) HD can vary in a range of about 40 nm to about 100 nm.

PDI is a representation of the distribution of size populations within a particle sample. The numerical value of PDI ranges from 0.0 for a perfectly uniform population within a particle sample to 1.0 for a highly polydisperse population within a particle sample. PDI values of 0.2 and below are deemed acceptable in practice for polymer-based nanoparticle materials. The calculations used for the determination of PDI are defined in the ISO standard documents 13321: 1996 E and ISO 22412:2008. PENP-MultiDots (4a) can have a substantially consistent PDI of about 0.1 to about 0.2.

Now, with primary reference to FIGS. 7A through 7E, TEM micrographs evidence that PENP-MultiDots (4a) can be loaded with QD (2a) having a range of emission wavelengths in the visible and near infrared spectrum while in the range retaining a substantially uniform and narrow size distribution. In particular embodiments, the PENP-MultiDots (4a) can be loaded with QD (2a) having emission wavelengths occurring in the range of about 420 nm to about 880 nm or upconverting nanoparticles. The illustrative examples of FIGS. 7A through 7E, evidence PENP-MultiDots (4a) having an emission wavelength of 420 nm (as shown the example of FIG. 7A), an emission wavelength of 575 nm (as shown the example of FIG. 7B), an emission wavelength of 610 nm (as shown by the example of FIG. 7C), and an emission wavelength of 655 nm (as shown by the example of FIG. 7D). A long felt but unresolved concern with nanocomposites is the lack of uniform and narrow size distribution between nanocomposites including QD (2a) having different emission wavelengths. As an illustrative example, QD (2a) that have an emission wavelength at 420 nm can be smaller in size than QD (2a) that have an emission wavelength at 610 nm. Additionally, the larger the QD (2a) the brighter the QD (2a) for a given composition. Moreover, under substantially similar methods of preparation, nanocomposites load a greater number of QD (2a) that have an emission wavelength at 420 nm as compared to QD (2a) that have an emission wavelength at 610 nm. These differences between QD (2a) of varying emission wavelength in regard to one or more of: size, brightness and loading affinity under similar methods of preparation can result in nanocomposites that correspondingly differ in size and brightness. Embodiments of the nanocomposites including QD (2a) having different emission wavelengths can be produced by the inventive method in a uniform and narrow size distribution by adjusting the QD inorganic metal mass to polymer mass ratio in the organic phase (OP) introduced into the aqueous phase (AP) during EHD mixing. In embodiments of the PENP-MultiDots (4a), the QD inorganic metal mass to polymer mass can be adjusted between 1:1 to 1:2 to produce PENP-MultiDots (4a) having uniform and narrow size distribution between nanocomposites containing QD (2a) having different emission wavelengths in the range of 40 nm to 500 nm and having substantially similar brightness. In embodiments of the PENP-MagDots (4b), the QD and SPION inorganic metal mass to polymer mass can be adjusted between 1:2 to 1:4 to produce PENP-MagDots (4b) having uniform and narrow size distribution between nanocomposites containing QD having different emission wavelengths in the range of 40 nm to 500 nm and having substantially similar brightness. It is not intended that these illustrative examples preclude other embodiments of PENP-MultiDots (4a) which can be produced, as above described, having other mono-wavelength emission, dual-wavelength emission, or more than dual-wavelength emission depending on the one or more QD (2a) encapsulated in the polymer (P) (3).

PENP-MagDots.

Superparamagnetic iron oxide nanoparticles ("SPION") (2b) are small synthetic particles of maghemite having an empirical formula of $Fe_2O_3$, $\gamma$-$Fe_2O_3$ and a molar mass 159.69 g/mol (CAS No. 1309-37-1) or magnetite having an empirical formula of $Fe_3O_4$ and a molar mass of 231.53 g/mol (CAS NO. 1317-61-9), or combinations thereof, with a core ranging from about 5 nm to about 30 nm in diameter. In addition, mixed oxides of iron with transition metal ions such as copper, cobalt, nickel, and manganese, are known to exhibit superparamagnetic properties and also fall into the category of SPION (2b). However, magnetite and maghemite nanoparticles are the most widely used SPION (2b) in various biomedical applications. SPIONS (2b) exhibit the phenomenon of "superparamagnetism." The particles that exhibit superparamagnetism, on application of an external magnetic field (15) (as shown in the example of FIG. 5), become magnetized up to their saturation magnetization, and on removal of the magnetic field, no longer exhibit any residual magnetic interaction. This property is size-dependent and generally arises when the size of nanoparticles reaches about 5 nm. At such a small size, these nanoparticles do not exhibit multiple domains as found in large magnets; on the other hand, they become a single magnetic domain and act as a "single super spin" that exhibits high magnetic susceptibility. Thus, on application of a magnetic field, these nanoparticles provide a stronger and more rapid magnetic response compared with bulk magnets with negligible remanence (residual magnetization) and coercivity (the field required to bring the magnetism to zero). Once the applied magnetic field is removed, the magnetic particles retain no residual magnetism at room temperature and are easily dispersed. Uncoated iron oxide NPs have very low solubility that can lead to precipitation due to gravitation forces and also a high rate of agglomeration under physiological conditions. Thus, to be used effectively, SPION can be capped with an amphiphilic coating.

In particular embodiments, SPION (2b) capped with a ligand (16), such as oleic acid, can have particle sizes in the range of about 5 nm to about 30 nm. Various SPION (2b) can be obtained from Ocean NanoTech, PN SOR05 to SOR30. Illustrative examples of embodiments, include SPION (2b) capped with oleic acid having particle sizes of 5 nm, 10 nm, 15 nm, and 20 nm. However, these illustrative SPION (2b) particle sizes are not intended to preclude the use of SPION (2b) having lesser or greater particle size, or combinations of SPION (2b) particle sizes, which can be used alone or in combination with one or more QD (2a) in embodiments of the PENP (4).

Typically, capped SPION (2b) in accordance with the invention reach a required level of water solubility and biocompatibility by surrounding the SPION (2b), or SPION/ QD (2a, 2b) combination(s), with a polymer (3). A polymer (3) encapsulation layer suitable for use with embodiments of the invention include PS-b-PEG-$NH_2$ obtained in Block 2I of the synthesis process, above described. Embodiments of the invention can be produced through the use of various combinations of one or more of: SPION (2b) or SPION/QD (2a, 2b), capping ligand (16), and PS-b-PEG-$NH_2$ having PS molecular weights ranging from about 1.5 kDa to about 40 kDa and PEG having molecular weights ranging from about 10 kDa to about 40 kDa.

An illustrative example of a scalable method of production PENP-MagDots (4b) by EHD can include one or more of: PS-b-PEG-$NH_2$ obtained in FIG. 2, Block 2I at 10 mg/mL into a first 1.5 mL tube. Introduce 13 µl of the desired SPION (2b) particle from 25 mg/mL in toluene (e.g. 20 nm) into a second 1.5 mL tube. Transfer 52 µl of acetone/ methanol (60/40) to the SPION in the second 1.5 mL tube. Mix by shaking. Centrifuge the second 1.5 mL tube containing the mixed SPION (2b) at 7000 RPM for 1 min. at about 25° C. (about 77° F.). Immediately remove supernatant with a 200 µl pipette. Immediately, transfer 13 µl of anhydrous tetrahydrofuran ("THF") to the second 1.5 mL tube containing the SPION (2b) and mix thoroughly with a pipette. Transfer 65 µl of a QD (2a) (from 5 mg/mL in toluene) into third 1.5 mL micro centrifuge tube. Transfer 130 µl of acetone/methanol (60/40 v/v) to the third 1.5 mL microcentrifuge tube containing the QD. Tilt to gently mix the QD (2a). Centrifuge the third 1.5 mL microcentrifuge tube containing QD at 7000 R.P.M. for 1 minute at 25° C. (about 77° F.). Remove the supernatant with 200 µl pipette. Transfer 65 µl of THF to the third 1.5 mL microcentrifuge tube. Mix thoroughly with an air displacement pipette. To a 4 mL vial, add 322 µL of THF. Transfer 13 µL of the SPION (2b) in THF contained in the second 1.5 µL microcentrifuge tube into the 4 mL vial. Optionally, transfer 65 µL of the QD (2a) in THF contained in the third 1.5 mL microcentrifuge tube into the 4 mL vial. Transfer 100 µL of the PS-b-PEG-$NH_2$ into the 4 mL vial to produce the OP for EHD.

Particular embodiments, EHD can be performed by cleaning the EHD mixing system syringe (11) three times with THF. Load about 0.5 mL of the OP into the syringe barrel (12). Mix the inorganics in the OP thoroughly while loading the syringe (11). Attach the syringe (11) to the syringe pump (15) and set the syringe pump (15) to generate a flow rate of the OP containing the inorganics from the syringe needle (14) in the range of about 11.00 mL/hr. to about 14.00 mL/hr. In particular embodiment the flow rate can be about 12.5 mL/hr. Prime the syringe needle (14) until a drop of the OP forms at the end of the syringe needle (14). Twice rinse a 20 mL glass vial (17) with distilled or deionized water (individually or collectively "DI water"). Introduce about 10 mL of DI water into the 20 mL glass vial (17). Submerge the syringe needle (14) into the 20 mL glass vial (17). Clean the negative electrode (19) by submerging in THF, wipe, and rinse with DI water. Place the negative electrode (19) into the AP contained in the 20 mL glass vial (17). Place the positive electrode (18) into the AP contained in the 20 mL glass vial (17). In particular embodiments the syringe needle (14), if electrically conductive, can act as the positive electrode (18). Observe that the positive electrode (18), the negative electrode (19), and the syringe needle (14) do not contact. Connect the positive lead (21) from the voltage source (20) to the positive electrode (18) or syringe needle (14) and connect the negative lead (22) from the voltage source (20) to the negative electrode (19). Verify that the power source delivers about −1000 V.

The EHD-PENP (4) produced by mixing the organic phase mixed with the DI water under influence of the electrical field can be concentrated using centrifugal filtration. The contents of the 20 mL glass vial (17) can be transferred to a 100 kDa cutoff centrifugal ultrafiltration column available from SigmaAldrich, PN UFC9010D Amicon® Ultra-15 Centrifugal Filter Unit. Centrifuge at 2000 RCF for 30 min. at about 25° C. (about 77° F.). Transfer EHD-PENP (4) from the centrifugal ultrafiltration column to a 1.5 mL microcentrifuge tube. Measure and record the EHD-NP volume. Transfer 5 μL of EHD-PENP (4) filtrate from the 1.5 mL microcentrifuge tube to a 1.5 mL tube and add 295 μl borate buffer. Transfer 290 μl of EHD-PENP (4) to a spectrophotometer cuvette. Measure and record optical density with spectrophotometer at 450 nm ($OD_{450}$).

The EHD-PENP filtrate may contain aggregates of PENP (4) or aggregates of PENP lacking a SPION (Sb) or a QD (2a) (collectively "aggregate"). The aggregates can be substantially removed from the EHD-NP filtrate to produce substantially pure PENP-MagDots (4b). As one example, a scalable size exclusion process to purify PENP-MagDots (4b) can include: place a magnetic particle separation column ("MPSC") in a magnetic field gradient (e.g. up to about 100-200 T/m). Transfer 300 μl of borate buffer into MPSC. Allow the borate buffer to pass through the MPSC. Introduce the EHD-NP filtrate into the MPSC in the magnetic field (23). Allow the filtrate liquid to pass through the MPSC. Transfer 300 μl of borate buffer into MPSC. Mix the EHD-NP in the borate buffer in the MPSC. Allow all of the borate buffer to pass through the MPSC. Extract the MPSC from the magnetic field gradient. Once the MPSC is extracted from the magnetic field gradient (23) the MPSC can no longer retain the PENP-MagDots (4b) which can then be eluted. Remove any liquid from MPSC tip. Place the MPSC in a PENP-MagDots (4b) collection tube labeled PENP-MagDots-Wavelength. Transfer 200 μl of borate buffer into the MPSC. Pipette to mix PENP-MagDots (4b) in the borate buffer in the MPSC. Collect PENP-MagDots (4b) into the PENP-MagDots-Wavelength collection tube. Mix collected PENP-MagDots (4b) thoroughly with an air displacement pipette. Measure and record the volume of the collected PENP-MagDots (4b). Combine 5 μl of PENP-MagDots (4b) and 295 μl of borate buffer. Transfer 290 μl of sample to spectrophotometer cuvette. Measure and record optical density with spectrophotometer at 450 nm ($OD_{450}$).

Now, with primary reference to FIGS. 8A through 8C including TEM micrographs illustrating PENP-MagDots (4b) produced by the above method loaded with SPION (2b), and optionally a combination of SPION (2b) and QD (2a) having emission wavelengths in the visible and near infrared spectrum. In the illustrative examples, PENP-MagDots (4b) include one or more QD (2a) having emission wavelengths of 610 nm, in combinations with 20 nm (as shown in the example of FIG. 8A), 15 nm (as shown in the example of 8B) and 5 nm (as shown in the example of FIG. 8C) SPION respectively. The morphology of PENP-MagDots (4b) produced by the above EHD-EM-NP method can be characterized by the use of TEM image and dynamic light scattering of the PENP-MagDots (4b) to determine HD and PDI, as above described.

Now, with primary reference to FIGS. 9A and 9B, comprising TEM micrographs illustrating PENP-MagDots (4b) produced in accordance with the above method. DLS can also be used in determining the size of PENP-MagDots (4b). During DLS measurement, a suspension of PENP-MagDots (4b) can be exposed to a light beam and as the incident light impinges on the PENP-MagDots (4b), the direction and intensity of the light beam can be altered due to scattering. PENP-MagDots (4b) in suspension are in constant random motion due to their kinetic energy, the variation of the intensity with time, therefore, contains information on that random motion and can be used to measure the diffusion coefficient of the particles. The HD of the PENP-MagDots $R_H$ can be calculated from its diffusion coefficient by the Stokes-Einstein equation $D_f = k_B T/6\pi\eta R_H$, where $k_B$ is the Boltzmann constant, T is the temperature of the suspension, and η is the viscosity of the surrounding media.

Now, with primary reference to FIG. 9A, including a TEM micrograph of PENP-MagDots (4b) prepared using a ratio of QD (2a):15 nm SPION (2b):polymer (P) (3) (5:5:20) ("PENP-MagDots15") and FIG. 9B including a TEM micrographs of PENP-MagDots (4b) prepared using a ratio of QD (2a):5 nm SPION (2b):polymer (3:5:20) ("PENP-MagDots 5") evidence that the brightness and magnetic susceptibility of the MagDot can be adjusted by loading different sized SPION. The PENP-MagDots15 produced using the ratio 5:5:20 can be more magnetic than the PENP-MagDots 5 using the 3:5:20 ratio. The PENP-MagDots 5 produced using the ratio 3:5:20 can be brighter than the PENP-MagDots 15 using the 5:5:20 ratio.

Now, with primary reference to FIG. 9C, nanoparticle tracking analysis (NTA) of each of the PENP-MagDots15 shown in the example of FIG. 9A can be illustrated as a plot of particle size versus particle concentration to evidence that the HD of each population can have a uniform size with a PDI of about 0.1 to about 0.2. The determined HD of the PENP-MagDots15 can be about 120 nm to about 140 nm and the determined HD of the PENP-MagDots5 can be about 180 nm to about 220 nm.

Based on the TEM analysis or DLS or NTA analysis, the HD of the PENP-MagDots (4b) produced by the above EHD method can vary depending on the parameters used during EHD and occur within a range of about 40 nm to about 500 nm, and evidence that PENP-MagDots (4b) populations evidence substantially uniform HD and a PDI of about 0.1 to about 0.2.

Now, with primary reference to FIG. 9D comprising a bar graph comparing the iron concentration of PENP-MagDots 5 and PENP-MagDots 15, evidence that PENP-MagDots 15 can be produced having a greater iron concentration than PENP-MagDots 5.

Now, with primary reference to FIG. 9E comprising a bar graph comparing the fluorescence of PENP-MagDots 5 and PENP-MagDots 15, evidence that PENP-MagDots 5 can be produced having a greater fluorescence than PENP-MagDots15.

Thus, by pre-selection of one or more of: SPION (2b) size, QD (2a), PS-b-PEG-NH$_2$ (3) which can include PS molecular weights ranging from about 1.5 kDa to about 40 kDa and PEG having molecular weights ranging from about 10 kDa to about 40 kDa, and parameters of EHD, and the ratio of QD:SPION:polymer numerous and varied embodiments of the PENP-MagDots (4b) can be produced having utility in a correspondingly numerous clinical and non-clinical applications.

Preparation of Antibodies.

Again, with primary reference to FIG. 1, the polymer nanomaterial encapsulation system (1) can further include the preparation of antibodies (Ab) (5). In particular embodiments, the PENP (4) produced by FNP, EHD, EM-NPa, self-assembly, or by other means, can be targets for site directed conjugation to antibodies (Ab) (5'). As one illustrative example, half-antibodies can be produced by preferential reduction of the disulfide bonds in the antibody hinge region to yield monovalent components with free thiol groups ("SH") that can be employed for site-directed conjugation to PENP, PENP-MultiDots, PENP-MagDots or combinations thereof. The reduced antibody fragments can be prepared by reacting 2-mercaptoethylamine hydrochloride (2-MEA), dithiothreitol, mercaptoethanol, or tris(2-carboxyethyl) phosphine (TCEP), to produce a reduced half-antibody as shown in Formula IX.

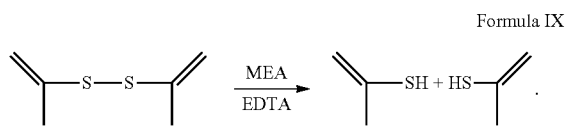

Formula IX

However, this example is not intended to preclude embodiments that may include one or more of: full antibody molecules or their F(ab')2, Fab', Fv, rIgF, Fc fragments obtained after pepsin or other enzymatic digestion, or combinations thereof.

A particular illustrative example of a scalable process to produce half-antibodies useful for conjugation to PENP (4), PENP-MultiDots (4a), and/or PENP-MagDots (4b) can include: preparing an antibody stock solution including Immunoglobulin G ("IgG") (0.5 mg/mL) in a buffer solution of 100 mM phosphate buffer saline ("PBS") with 10 mM ethylenediaminetetraacetic acid disodium salt dihydrate ("EDTA") at pH 7.4 ("PBS buffer solution"). An aliquot of 160 µl of the IgG stock solution can be transferred to a first 1.5 mL tube. 2-MEA.HCl having a linear formula of HSCH$_2$CH$_2$NH$_2$·HCl and a molecular weight of 113.60 (CAS NO: 156-57-0) can be obtained from Fisher Scientific PN AAA1437714. In a second 1.5 mL tube, 15 mg of 2-MEA.HCl can be dissolved in 264 µl PBS buffer solution by pipetting. Transfer 5.0 µl of the 2-MEA.HCL solution, respectively, to the 160 µl of the IgG stock solution in the first 1.5 mL tube, vortex, and place 1.5 mL tube containing the IgG solution in a water bath at 37° C. (about 98.6° F.) for 90 min.

The resulting reduced antibody product (also, referred to as "half-antibody product") (5) may require desalting and a buffer exchange. Desalting removes unreacted MEA contaminants from the half-antibody product while exchanging the half-antibodies into reaction buffer for conjugation to the PENP (4), PENP-MultiDots (4a), and/or PENP-MagDots (4b). An illustrative example of a scalable procedure for desalting and buffer exchange can include utilization of ZEBA™ spin desalting columns obtained from ThermoFisher Scientific, PN 89883, or equivalents thereof. A pair of desalting columns can each be prepared by removing the bottom closure and placing the columns in a 1.5 mL collection tube. Centrifuge at 1500×g for 1 min. to remove storage solution from the desalting column resin. Add 300 µl of 1×100 mM Sodium Phosphate, 1 mM EDTA in water at pH: 6.95-7 (rinse buffer") or appropriate buffer to the top of the resin bed and centrifuge at 1500 RFC for 1 min. Discard flow-through from collection tube. Repeat addition of 300 µl of 1× rinse buffer two additional times, discarding buffer from the collection tube each time.

The desalting column can now be loaded with the reduced antibody (5) product by placing the first equilibrated desalting column into a first 1.5 mL collection tube marked reduced antibody 1 ("R-Ab-1"), remove the cap from the top of the first desalting column and slowly apply up to a 160 µl reduced antibody product to the center of the compact resin bed. For sample volumes less than 70 µl, apply 15 µl buffer (stacker) to the top of the resin bed after the sample has fully absorbed to ensure maximal protein recovery. Centrifuge at 1500 RCF for 2 min. at 15° C. to 20° C. (59° F. to 68° F.) to collect desalted reduced antibody product. Place the second equilibrated desalting column into a second 1.5 mL collection tube marked reduced antibody 1 ("R-Ab-2"), remove the cap from the top of the second equilibrated desalting column. Transfer the collected reduced antibody (5) product from collection tube R-Ab-1, to the top of the second desalting column. Centrifuge at 1500 RCF for 2 min. at 15° C. to 20° C. (59° F. to 68° F.) to collect desalted reduced antibody product in collection tube R-Ab-2. Cap collection tube R-Ab-2 and place at RT.

Preparation of Half-Antibody-Polymer Nanocomposite Conjugates.

Now, with primary reference to FIG. 1, the polymer nanomaterial encapsulation system (1) can further include the surface functionalization of PENP (4), PENP-MultiDots (4a), and/or PENP-MagDots (4b) by addition of the reduced antibody product FIG. 1, Block 1 D. As a basis for modification, chemical groups such as amines, carboxylates, thiols, or other reactive groups can be introduced into the PENP (4), PENP-MultiDots (4a), and/or PENP-MagDots (4b) during synthesis, as above described. These groups can be targeted by heterobifunctional chemical cross-linkers (10) including reactive chemical groups connected by spacer arms (as examples: alkane, polyethylene glycol, cleavable disulfide spacers) having various lengths and functions, imparting flexibility, solubility, or other desirable characteristics to the functionalized PENP (4), PENP-MultiDots (4a), and/or PENP-MagDots (4b). As examples, PENP functional group(s) (9) can be reacted with the first reactive group (10') of the heterobifunctional chemical cross-linkers (10). As illustrative examples, where the functional group (9) of the PENP (4), PENP-MultiDots (4a), and/or PENP-MagDots (4b) comprises an amine, the amine can be reacted with a succinimidyl esters to form amide bonds, or comprises a carboxylate, the carboxylate can be reacted with carbodiimides to produce O-acylisourea intermediates that can be reacted with amines to form amide bonds, or comprise a thiol, the thiol can be reacted with maleimide to form thioether bonds. The reduced antibody (5) product can be reacted with the second reactive group (10") of the heterobifunctional chemical cross-linker (as shown in the example of FIG. 4C). For example, the second reactive group (10") of the heterobifunctional chemical cross-linker (10) can comprise a maleimide which can react with the sulfhydryl of the half anti-body (5) to form a thioether bond.

In particular embodiments, both the reactive group associated with the PENP (4) can be modified by reaction with the first reactive group (10a') of a first heterobifunctional cross-linker (10a) and the reduced antibody (5) product can modified by reaction with the first reactive group (10b') of a second heterobifunctional chemical cross-linker (10b). The first and second chemical cross-linkers (10a, 10b) can be selected to include second reactive groups (10a", 10b") that remain stable in physiological aqueous buffers and upon admixture proceed with fast kinetics and high selectivity to create a covalent bond.

In particular embodiments, the reduced antibody (5) product in collection tube R-Ab-2 can be modified for subsequent conjugation to PENP (4) by reaction of the free sulfhydryl group of the half-antibody (5) with a first reactive group (10a') comprising a malcimide of a first heterobifunctional cross-linker (10a) to form a thioether bond. In an illustrative example, the first heterobifunctional cross-linker (10a) can comprise sulfo trans-cyclooctene maleimide ("Sulfo-TCO Maleimide") having a linear formula $C_{17}H_{27}N_3O_8S$ (CAS No. n/a) and a molecular weight of 457.50 g/mol can be obtained from Click Chemistry Tools, PN 1355 comprising Formula X.

Formula X

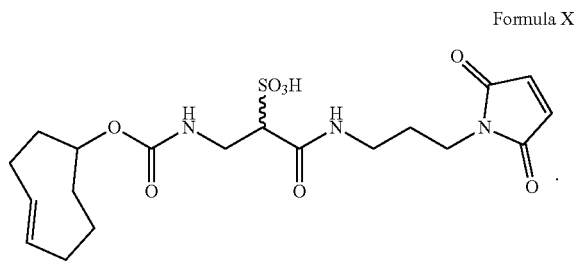 [SMILES: O=C(NCC(C(=O)NCCCN1C(=O)C=CC1=O)S(=O)(=O)O)OC1CC/C=C/CCC1]

Sulfo TCO-Maleimide comprises a water-soluble reagent that enables incorporation of the TCO moiety onto thiol-containing half-antibody. The maleimide group specifically reacts with the sulfhydryl group ("SH") at pH 6.5 to 7.5 to form a stable thioether bond. The hydrophilic sulfonated spacer arm greatly improves water solubility of Sulfo TCO antibody ("Sulfo-TCO-Ab") comprising the Formula XI.

Formula XI

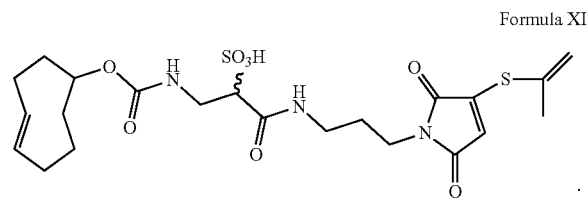 [SMILES: C=C(C)SC1=CC(=O)N(CCCNC(=O)C(CNC(=O)OC2CC/C=C/CCC2)S(=O)(=O)O)C1=O]

An illustrative example of a scalable process to produce the Sulfo-TCO-Ab useful for conjugation to PENP can include one or more of: Remove a tube containing 0.1 mg Sulfo-TCO-maleimide from −20° C. (−4° F.) and bring to RT over 15 min. Add 46.4 µl of anhydrous dimethysufoxide ("DMSO") having a linear formula $C_2H_6OS$ and a molecular weight of 78.13 g/mol. (CAS No. 67-68-5) to 0.1 mg Sulfo-TCO-maleimide. Vortex the Sulfo-TCO-maleimide in the tube for 10 min. to ensure dissolution in the DMSO. Repeatedly mix the Sulfo-TCO-maleimide in DMSO via pipette set to 60 µl. Add 5 µl or 10 µl of Sulfo-TCO-maleimide to the R-Ab-2 tube containing the reduced antibody (5). Discard the remaining Sulfo-TCO-maleimide. Relabel the tube containing the Sulfo-TCO-Ab. Cap and vortex the tube containing the Sulfo-TCO-Ab. Place the Sulfo-TCO-Ab tube at 4° C. (39.2° F.) for 20-24 hr.

The PENP (4) products above described can be reacted with a first reactive group of a second heterobifunctional cross-linker. The modified PENP (4) can then be associated with one or more target moieties (24), including one or more of: cells, cell organelles, proteins, peptides, amino acids, oligonucleotides, ligands, or linkers by selective reaction of the second reactive group with the corresponding function groups within the target moiety (24).

In particular embodiments, the second heterobifunctional cross-linker (10b) can comprise methyltetrazine polyethylene glycol-4-N-hydroxysuccinimide ester ("TZ-PEG$_4$-NHS ester") having a linear formula $C_{24}H_{31}N_5O_9$ having a molecular weight of 533.53 g/mol (CAS NO. 182907-92-1) comprising Formula XII.

Formula XII

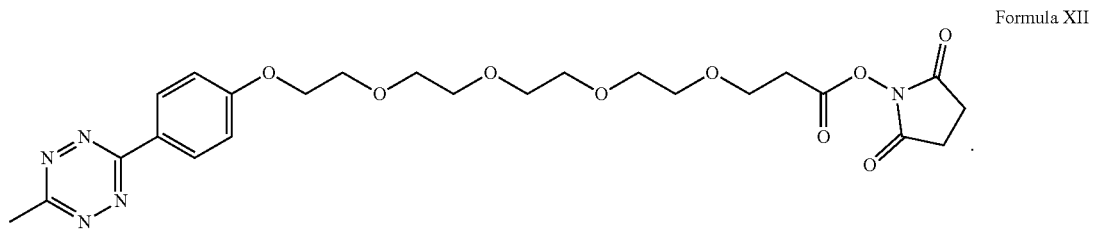 [SMILES: Cc1nnc(-c2ccc(OCCOCCOCCOCCOCCC(=O)ON3C(=O)CCC3=O)cc2)nn1]

An illustrative example, the TZ-PEG4-NHS ester comprising Formula XIII can be reacted with the functional group (9) of the multi-arm PEG-NH$_2$ (3) comprising multiple amine as shown in Formula IV or Formula V of the PENP (4) to produce PENP-PEG$_4$-TZ comprising Formula XIII.

Formula XIII

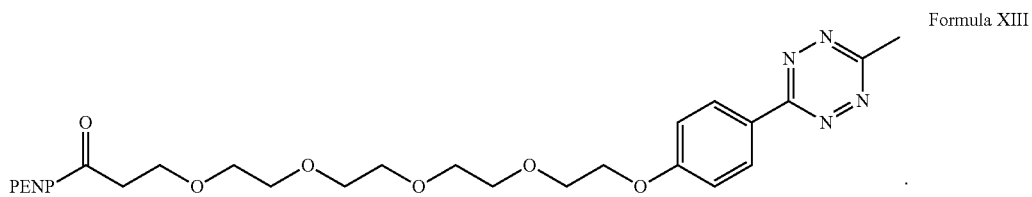

As one example, a scalable process to produce the PENP-PEG$_4$-TZ of Formula XIII using the PENP (4) functional group (9) comprising an amine of the multi-arm PEG-NH$_2$ (3) shown in Formula IV or Formula V can include one or more of: bring 1 mg of TZ-PEG-NHS ester to RT over approximately 15 min. Transfer 93.7 µl or 375 µl of anhydrous DMSO to TZ-PEG4-NHS ester to produce 20 mM or 5 mM TZ-PEG4-NHS in DMSO. Mix TZ-PEG4-NHS ester in DMSO by pipette for complete dissolution of TZ-PEG4-NHS ester in DMSO. Label 1.5 mL tube as PENP-Wavelength-TZ. Transfer PENP into PENP-Wavelength-TZ tube (120 µl of PENP-MagDots or 80 µl of PENP-MultiDots). In PENP-MultiDots (4a) embodiments about 30 nmol of amine can be activated by reaction with about 70 nmol of TZ-PEG4-NHS ester and in PENP-MagDot (4b) embodiments about 120 nmol of amine can be activated by reaction with 70 nmol of TZ-PEG4-NHS ester. Pipette 3.5 µL of 20 mM TZ-PEG4-NHS ester into the PENP-MultiDot-Wavelength-TZ tube or 15 µl of 5 mM TZ-PEG4-NHS ester into the PENP-MagDot-Wavelength-TZ tube. Mix thoroughly with an air displacement pipette. React at RT for 2 hrs.

In particular embodiments the PENP-PEG$_4$-TZ comprising Formula XIII can be reacted with Sulfo-TCO-Ab comprising the Formula XI in an inverse-electron demand Diels-Alder [4+2] cycloaddition reaction of TCO with TZ to form a dihydropyridazine bond to produce conjugate PENP-Antibodies (6) ("PENP-Ab") comprising Formula XIV including but not limited to PENP-MultiDots (4a) shown in the example of FIG. 4A or PENP-MagDots (4b) as shown in the example of FIG. 4B, where R$_1$ comprises PENP and where R$_2$ comprises an Ab.

Formula XIV

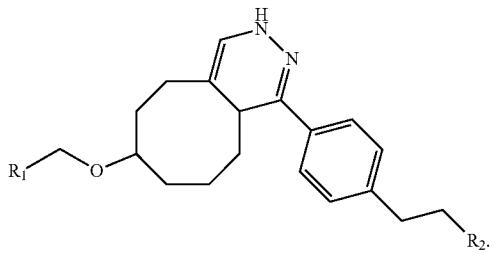

As one example, a scalable process to produce the PENP-Ab (6) of Formula XIV using PENP-PEG$_4$-TZ (PENP-MagDots-PEG$_4$-TZ or PENP-MultiDots-PEG$_4$-TZ) and Sulfo-TCO-Ab can include a pair of desalting columns (as a non-limiting example Zeba™ desalting columns) each prepared by removing the bottom closure and placing each of the pair of desalting columns in a 1.5 mL collection tube. Centrifuge at 1500×g from 1 min. to remove storage solution from the desalting column resin. Add 300 µL of 1× rinse buffer or appropriate buffer to the top of the resin bed and centrifuge at 1500 RFC for 1 minute. Discard flow-through from the respective collection tubes. Repeat addition of 300 µL of 1× rinse buffer (pH 6.0) two additional times, discarding buffer from the respective collection tubes each time. Transfer the PENP-PEG4-TZ to the first of the pair of desalting columns. Transfer the Sulfo-TCO-Ab to the second of the pair of desalting columns. Centrifuge the first and second desalting columns at 1500 RCF for 2 min. at 15° C. to 20° C. (59° F. to 68° F.) to collect PENP-PEG4-TZ and Sulfo-TCO-Ab products post excess unconjugated linker removal. Mix the desalted PENP-PEG4-T7 (120 µL PENP-MagDots or 80 µL PENP-MultiDot) in the first collection tube by pipette. Transfer the desalted 160 µL (80 µg) Sulfo-TCO-Ab from the second collection tube into the PENP-PEG4-TZ in the first collection tube. Let react for 24 hrs. at 4° C. (39.2° F.) to produce PENP-Ab (PENP-MagDots-Ab or PENP-MultiDots-Ab).

Subsequent to conjugation, the resulting PENP-Ab (6) product can be purified. As one example, a scalable size exclusion process to purify PENP-MultiDots-Ab can include: label a 1.5 mL microcentrifuge tube as "PENP-MultiDots-Ab-Wavelength". Introduce 3 mL of gel filtration resin (e.g. Sephacryl® available from SigmaAldrich, PN S400HR) into 3 mL borate buffer saline (50 mM sodium borate, 100 mM sodium phosphate, 7.3-7.5 pH ("borate buffer")) ("BBS"). Transfer the suspension of gel filtration resin into a size exclusion column ("SEC"). Slowly pipette PENP-MultiDots-Ab (6a) solution to the sides of the SEC. Connect an air syringe to the SEC. Push 1 mL of air into the SEC via the air syringe. Allow the PENP-MultiDots-Ab (6a) solution to move into the gel filtration resin. Remove air syringe from the SEC. Pipette 200 µl BBS buffer to the sides of the SEC. Reconnect the air syringe to the SEC. Push 1 mL of air into the SEC via the air syringe. Allow the PENP-MultiDots-Ab (6a) solution to move into SEC packing. Remove the air syringe from SEC. Pipette 1000 µl BBS to the sides of the SEC. Reconnect the air syringe to the SEC. Reduce ambient light incident upon the SEC. Direct ultraviolet light ("UV light") incident upon SEC. Push 1 mL of air into the SEC via the air syringe. Begin collection of BBS eluent from SEC. Upon detection of first fluorescent drop from SEC, collect fluorescent drops 2 through 5 in PENP-MultiDots-Ab-Wavelength collection tube. Mix collected fluorescent drops sample with a pipette. Remove the air syringe, dispose the gel filtration resin and clean the SEC.

As one example, a scalable size exclusion process to purify PENP-MagDots-Ab (6b) can include: mix PENP-MagDots-Ab (6b) in conjugation buffer thoroughly with an air displacement pipette. Place a MPSC in a magnetic field gradient (e.g. up to about 100-200 T/m). Introduce the PENP-MagDots-Ab (6b) in conjugation buffer into the MPSC. Allow the conjugation buffer to pass through the MPSC. Transfer 300 µL of BBS into MPSC. Pipette to mix PENP-MagDots-Ab in reaction buffer in the MPSC. Allow the reaction buffer to pass through the MPSC. Transfer 300 µL of reaction buffer into the MPSC. Pipette to mix PENP-MagDots-Ab (6b) in reaction buffer in the MPSC. Allow the reaction buffer to pass through the MPSC. Remove any reaction buffer from tip of the MPSC. Extract the MPSC from the magnetic field gradient. Once the MPSC is extracted from the magnetic field gradient, the MPSC can no longer retain the PENP-MagDots-Ab (6b) and the PENP-MagDots-Ab (6b) can be eluted. Place the MPSC in a PENP-MagDots-Ab (6b) collection tube labeled PENP-MagDots-Ab-. Transfer 200 µl of reaction buffer into the MPSC. Pipette to mix PENP-MagDots-Ab (6b) in reaction buffer in the MPSC. Collect PENP-MagDots-Ab (6b) into the MagD-Antibody-Date collection tube. Mix collected PENP-MagDots-Ab (6b) thoroughly with an air displacement pipette.

Cell Labelling and Flow Cytometry Utilizing PENP-MultiDots-Ab.

PENP-MultiDots-Ab (6a) can effectively and specifically label target moieties (24) comprising cellular targets (24'). Single particle imaging, cellular imaging, or flow cytometry using PENP-MultiDots-Ab (6a) labeled cellular targets (24') evidence very high fluorescence intensity compared to labeling cellular targets (24') with conventional dyes. The PENP- MultiDots-Ab (6a) can effectively and specifically label cell surface receptors and subcellular structures in both live or fixed cells without any detectable non-specific binding. Flow cytometry can be performed to evaluate PENP-MultiDots-Ab (6a) performance and to show the high cellular label brightness compared to conventional dyes and quantum dot probes.

As one illustrative example of PENP-MultiDots-Ab (6a) labeling of cellular targets (24'), peripheral blood mononuclear cells ("PBMC") (24') can be labeled using PENP-MultiDots-Ab (4a). A scalable method of labeling PBMC with PENP-MultiDots-Ab (6a) can include one or more of: diluting peripheral blood as an iso-osmatic solution 50:50 with Hank's balanced salt solution ("HBSS") (SigmaAldrich, PN H6648). Diluted peripheral blood can be layered over a Ficoll-Hypaque gradient (density=1.077 g/cm$^3$) and centrifuged at 1350 RPM for 30 min. without brake. Serum can be aspirated and discarded. PBMC can be removed and transferred to another collection tube and washed with PBS. The PBMC pellet can be resuspended in 10 mL PBS and cell counts performed on a hemacytometer. A million PBMC (24') in 200 μl of PBS can be placed in a 12×75 mm flow cytometry tube to which 10 μl of PENP-MultiDots-mouse anti human CD3 (6a) having a 610 nm emission wavelength was added. PBMC (24') and PENP-MultiDots-mouse anti human CD3 (6a) incubated for 25 min. at RT. After expiration of the incubation period, 500 μl of additional PBS can be added to the PENP-MultiDots-mouse anti human CD3 bound PBMC (7) ("PENP-MultiDots-mouse anti human CD3-PBMC"). The PENP-MultiDots-mouse anti human CD3-PBMC (7) were centrifuged for 7 min. at 1800 RPM at RT. The supernatant can be discarded and the PBMC/PENP-MultiDots-mouse anti human CD3-PBMC (7) can be resuspended in 400 μl of PBS for flow cytometry analysis (8) for detection of PENP-MultiDots-mouse anti human CD3-PBMC (7) population using a Cytek Northern Lights spectral flow cytometer. The CD3 protein complex can be an important T cell marker for the classification of malignant lymphomas and leukemias (T cell neoplasms). CD3 can also be used for the identification of T cells in coeliac disease, lymphocytic colitis and collagenous colitis.

Now, with primary reference to FIG. 10A, the univariant histogram (florescence intensity versus particle number) depicts detection of PENP-MultiDots-mouse anti human CD4-PBMC (7) population ("Peak M1") in a sample of PBMC/PENP-MultiDots-mouse anti human CD4-PBMC (7) obtained by the method above described. The histogram evidences that 38.41% of the cells in the sample can be identified as the PENP-MultiDots-mouse anti human CD4-PBMC (7) population within the sample. In particular embodiments, the PENP-MultiDots-mouse anti human CD4-PBMC (7) population can be sorted and isolated for further analysis.

Now, with primary reference to FIG. 10B, the univariant histogram (florescence intensity versus particle number) depicts detection of PENP-MultiDots-mouse anti human CD3-PBMC (7) population ("Peak M1") prepared in accordance with the methods above described. The histogram evidences that 50.09% of the cells in the sample can be identified as the PENP-MultiDots-mouse anti human CD3-PBMC (7) population within the sample.

PENP-MagDots-Ab (6b) can also effectively and specifically label cellular targets (24'). Single particle imaging, cellular imaging, or flow cytometry analysis (8) using PENP-MagDots-Ab (6b) labeled cellular targets (24') evidence very high fluorescence intensity compared to labeling cellular targets (24') with conventional dyes or quantum dots. The PENP-MagDots-Ab (6b) can effectively and specifically label cell surface receptors and subcellular structures in both live or fixed cells without any detectable non-specific binding. Flow cytometry (8) can be performed to evaluate PENP-MagDots-Ab (6b) performance and to show the high cellular label brightness compared to conventional dyes and quantum dot probes.

As one illustrative example of PENP-MagDots-Ab (6b) labeling of cellular targets (24'), peripheral blood mononuclear cells ("PBMC") (24') can be labeled using PENP-MagDots-Ab (6b). As one example, a scalable method can include one or more of: diluting peripheral blood as an iso-osmatic solution 50:50 with Hank's balanced salt solution ("HBSS") (SigmaAldrich, PN H6648). Diluted peripheral blood can be layered over a Ficoll-Hypaque gradient (density=1.077 g/cm$^3$) and centrifuged at 1350 RPM for 30 min. without brake. Serum can be aspirated and discarded. PBMC can be removed and transferred to a PBMC collection tube and washed with PBS. The PBMC pellet can be resuspended in 10 mL PBS and cell counts performed on a hemacytometer. A million PBMC (7) in 200 μl of PBS can be introduced into a 12×75 mm flow cytometry tube to which 20 μL of PENP-MagDots-mouse anti human CD3 (6b) having a 610 emission spectrum were added. PBMC and PENP-MagDots-mouse anti human CD3 (6b) are incubated for 25 min. at RT. After expiration of the incubation period, 200 μl of additional PBS can be added to the PENP-MagDots-mouse anti human CD3 bound PBMC (7) ("PENP-MagDots-mouse anti human CD3-PBMC") in the flow cytometry tube. Place the flow cytometry tube containing PENP-MagDots-mouse anti human CD3-PBMC (7) in PBS in a magnetic field gradient (23) (e.g. up to about 100-200 T/m). After expiration of 15 min., the nonmagnetic fraction can be aspirated from the flow cytometry tube and placed a nonmagnetic fraction collection tube. The flow cytometry tube containing the magnetically retained PENP-MagDots-mouse anti human CD3-PBMC (7) can be removed from the magnetic field gradient and the PENP-MagDots-mouse anti human CD3-PBMC (7) can be resuspended in 400 μl PBS. The PBMC/PENP-MagDots-mouse anti human CD3 reaction solution prior to magnetic separation, the nonmagnetic fraction after magnetic separation, and the PENP-MagDots-mouse anti human CD3-PBMC fraction after magnetic separation, were each analyzed by flow cytometer (8).

Now, referring primarily to FIGS. 11A through 11C, which depict bivariant dot plots (forward scatter area versus forward scatter height) obtained by flow cytometry analysis (8) of each of the PBMC/PENP-MagDots-mouse anti human CD3 reaction solution prior to magnetic separation (as shown by the example of FIG. 11A), the non-magnetic fraction after magnetic separation (as shown by the example of FIG. 11B), and the PENP-MagDots-mouse anti human CD3-PBMC fraction after magnetic separation (as shown by the example of FIG. 11C). The flow cytometry dot plots evidence the proportion of CD3 negative cells to CD3 positive cells. As evidenced by FIG. 11A, the PBMC/PENP-MagDots-mouse anti human CD3 reaction solution prior to magnetic separation contains 51.17% CD3 negative cells and 48.76% CD3 positive cells. FIGS. 11B and 11C, evidence that after magnetic separation the non-magnetic fraction contains largely CD3 negative cells 97.29% and very few CD3 positive cells 2.71%, whereas by contrast, FIG. 11C evidence that the PENP-MagDots-mouse anti human CD3-PBMC fraction after magnetic separation includes very few CD3 negative cells 2.60% and largely CD3 positive cells 97.37%. This evidence the substantial advantage of using PENP-MagDots-Ab (6b) to capture and purify cellular targets (24').

Now, referring primarily to FIGS. 12A through 12C which illustrate labeling of Hawaiian Bobtail Squid (*Euprymna scolopes*) hemocytes with PENP-MagDots. Adult Bobtail Squid can be incubated for 3 hr. with 100 uL of PENP-MagDots containing a QD having an emission wavelength of 610 nm. The images evidence that Hawaiian Bobtail Squid (*Euprymna scolopes*) hemocytes passively uptake PENP-MagDots 610 nm.

As can be easily understood from the foregoing, the basic concepts of the present invention may be embodied in a variety of ways. The invention involves numerous and varied embodiments of polymer encapsulated nanoparticles and methods for making and using such a polymer encapsulated nanoparticles.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of an "encapsulated nanoparticle" should be understood to encompass disclosure of the act of "encapsulating a nanoparticle"—whether explicitly discussed or not—and, conversely, were there effectively disclosure of the act of "encapsulating a nanoparticle", such a disclosure should be understood to encompass disclosure of a "encapsulated nanoparticle" and even a "means for encapsulating a nanoparticle." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Thus, the applicant(s) should be understood to claim at least: i) each of the polymer encapsulated nanoparticles herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon. The elements following an open transitional phrase such as "comprising" may in the alternative be claimed with a closed transitional phrase such as "consisting essentially of" or "consisting of" whether or not explicitly indicated the description portion of the specification.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A nanocomposite, comprising:
    an amphiphile having a hydrophobic region and a hydrophilic region, said amphiphile comprises polystyrene-b-polyethylene glycol including a functional group, wherein said polystyrene-b-polyethylene glycol includes a polystyrene block and a polyethylene glycol block including a branched polyethylene glycol selected from the group of: a four arm polyethylene glycol, a six arm polyethylene glycol and an eight arm polyethylene glycol; and
    at least one quantum dot and at least one magnetic particle encapsulated by association with said hydrophobic region of said amphiphile.

2. The nanocomposite of claim 1, wherein said at least one quantum dot has a core comprising cadmium sulfide and a shell of zinc sulfide and has an emission wavelength selected from the group consisting of 420 nm, 440 nm, and 460 nm, wherein said at least one quantum has a diameter occurring in the range of about 5 nm to about 8 nm.

3. The nanocomposite of claim 1, wherein said at least one quantum dot has a core comprising cadmium sulfide selenide and a shell of zinc sulfide and has an emission wavelength selected from the group consisting of 480 nm, 500 nm, and 520 nm, wherein said at least one quantum has a diameter occurring in the range of about 4 nm to about 6 nm.

4. The nanocomposite of claim 1, wherein said at least one quantum dot has a core comprising cadmium selenide and a shell of zinc sulfide and has an emission wavelength selected from the group consisting of 540 nm, 560 nm, 580 nm, and 600 nm, 620 nm, 640 nm, and 660 nm, wherein said at least one quantum has a diameter occurring in the range of about 4 nm to about 8 nm.

5. The nanocomposite of claim 1, wherein said at least one quantum dot has a core comprising cadmium telluride and a shell of zinc sulfide and has an emission wavelength selected from the group consisting of 680 nm and 700 nm, wherein said at least one quantum has a diameter occurring in the range of about 6 nm to about 7 nm.

6. The nanocomposite of claim 1, wherein said at least one quantum dot has a core comprising cadmium selenide telluride and a shell of zinc sulfide and has an emission wavelength selected from the group consisting of 720 nm, 740 nm, 760 nm, 780 nm, 800 nm, 820 nm, 840 nm, 860 nm, and 880 nm, wherein said at least one quantum has a diameter occurring in the range of about 4.5 nm to about 12 nm.

7. The nanocomposite of claim 1, wherein said at least one quantum dot has a core comprising copper indium zinc sulfide and a shell of zinc sulfide and has an emission wavelength selected from the group consisting of 540 nm, 560 nm, 580 nm, 600 nm, 620 nm, 640 nm, 840 nm, and 669 nm, wherein said at least one quantum has a diameter occurring in the range of about 3.5 nm to about 4 nm.

8. The nanocomposite of claim 1, wherein said at least one quantum dot has a core comprising lead sulfide and a shell of cadmium sulfide and has an emission wavelength selected from the group consisting of 900 nm, 920 nm, 940 nm, 960 nm, 980 nm, and 1000 nm, wherein said at least one quantum has a diameter occurring in the range of about 3.5 nm to about 5 nm.

9. The nanocomposite of claim 1, wherein said at least one magnetic particle has a mean particle diameter occurring in the range of about 5 nm to about 20 nm.

10. The nanocomposite of claim 9, wherein said at least one magnetic particle has a mean particle diameter selected from the group consisting of: 5 nm, 10 nm, 15 nm, 20 nm.

11. The nanocomposite of claim 10, wherein said magnetic particle comprises one or more of magnetite and maghemite.

12. The nanocomposite of claim 10, wherein said magnetic particle comprises a superparamagnetic iron oxide nanoparticle.

13. The nanocomposite of claim 1, wherein said polystyrene-b-polyethylene glycol has a polystyrene block having a molecular weight occurring in the range of about 1.5 kDa to about 40 kDa.

14. The nanocomposite of claim 1, wherein said polystyrene-b-polyethylene glycol has a polyethylene glycol block having a molecular weight occurring in the range of about 10 kDa to about 40 kDa.

15. The nanocomposite of claim 1, wherein said polystyrene-b-polyethylene glycol has said polystyrene block having a molecular weight occurring in the range of about 1.5 kDa to about 40 kDa and said polyethylene glycol block having a molecular weight occurring in the range of about 10 kDa to about 40 kDa, and combinations thereof.

16. The nanocomposite of claim 1, wherein said polystyrene-b-polyethylene glycol, said at least one quantum dot, and said at least one magnetic particle are soluble in a water-miscible nonpolar aprotic solvent, said polystyrene-b-polyethylene glycol, said at least one quantum dot, and said at least one magnetic particle in said water-miscible nonpolar aprotic solvent nanoprecipitate upon transfer into an aqueous phase under influence of an electrical field.

17. The nanocomposite of claim 16, wherein said mass concentration of said at least one quantum dot and said at least one magnetic particle to a mass concentration of said polystyrene-b-polyethylene glycol in said organic phase comprises a ratio of about 1:1 to about 1:4.

18. The nanocomposite of claim 17, wherein said mass concentration of said at least one quantum dot and said at least one magnetic particle in said organic phase is adjustable within said ratio to alter brightness of said nanocomposite when under an external stimulus.

19. The nanocomposite of claim 17, wherein said mass concentration of said at least one quantum dot and said at least one magnetic particle to said mass concentration of said polystyrene-b-polyethylene glycol is adjustable within said ratio affords a uniform hydrodynamic diameter of said nanocomposite occurring in a range of about 40 nanometers to about 1000 nanometers.

20. The nanocomposite of claim 17, wherein said mass concentration of said at least one quantum dot and said at least one magnetic particle to said mass concentration of said polystyrene-b-polyethylene glycol is adjustable by altering mass concentration of said polystyrene block.

21. The nanocomposite of claim 20, wherein said mass concentration of said polystyrene-b-polyethylene glycol is adjustable by altering mass concentration of said polyethylene glycol block.

22. The nanocomposite of claim 20, wherein said mass concentration of said polystyrene-b-polyethylene glycol is adjustable by selection of said polyethylene glycol block from the group of: said 4-arm polyethylene glycol, said six arm polyethylene and said 8-arm polyethylene glycol.

23. The nanocomposite of claim 16, wherein said polystyrene-b-polyethylene glycol, said at least one quantum dot, and said at least one magnetic particle have a concentration in combination of about 0.1 mg/mL to about 5.0 mg/mL.

24. The nanocomposite of claim 23, wherein said organic phase has a concentration in said aqueous phase of about 0.2 v/v to about 1 v/v.

25. The nanocomposite of claim 1, further comprising a ligand bound to said at least one said quantum dot and to said at least one magnetic particle, wherein said ligand has a mass relative to said combined mass of said at least one said quantum dot and said at least one magnetic particle occurs in a range of about 10 percent to about 40 percent.

26. The nanocomposite of claim 25, wherein said ligand comprises oleic acid or oleylamine, and combinations thereof.

27. The nanocomposite of claim 26, wherein said oleic acid has a mass relative to said combined mass of said at least one said quantum dot and said at least one magnetic particle is not less than 10 percent and comprises not greater than 40 percent.

28. The nanocomposite of claim 1, further comprising an agent that binds to said functional group, wherein said agent is selected from the group consisting of: polyethylene glycol, an antibody, a half antibody, an antibody fragment, a fluorescent probe, an aptamer, a vitamin, a cell surface receptor, a cell coat, a protein, a peptide, a radioactive isotope, a contrast medium, a surface charge modifier, a lectin, and combinations thereof.

29. The nanocomposite of claim 1, further comprising a linker bound to said functional group of said nanocomposite.

30. The nanocomposite of claim 29, wherein said linker comprises a heterobifunctional linker having a first reactive group adapted to react with said functional group of said amphiphile encapsulating said nanoparticle and having a second reactive group adapted to react with an agent.

31. The nanocomposite of claim 30, wherein said functional group comprises one or more of an acrylate, a maleimide, a vinylsulfone, an azide, a biotin, a carboxyl, a thiol, an alkyne, a hydrazide, a N-hydroxysuccinimide ester, a nitrophenyl carbonate, an amine, a carboxylate, and combinations thereof.

32. The nanocomposite of claim 31, wherein said functional group comprises an amine and said first reactive group of said heterobifunctional linker comprises a succinimidyl carboxymethyl ester.

33. The nanocomposite of claim 32, wherein said linker is selected from the group consisting of: acrylate polyethylene glycol succinimidyl carboxmethyl ester, biotin polyethylene glycol succinimidyl carboxmethyl ester, maleimide polyethylene glycol succinimidyl carboxmethyl ester, azide polyethylene glycol succinimidyl carboxmethyl ester, and combinations thereof.

34. The nanocomposite of claim 32, wherein said second reactive group is selected from the group consisting of: an acrylate, a maleimide, a vinylsulfone, and azide, a biotin, an amine, a carboxylic acid, a thiol, an n-hydroxysuccinimide ester, an alkyne, a hydrazide, and 4-hydroxy-3-nitrophenylacetyl-epsilon-aminocaproic acid anion, methyltetrazine polyethylene glycol4-N-hydroxysuccinimide ester, and combinations thereof.

35. The nanocomposite of claim 30, further comprising an agent that binds to said second reactive group, wherein said agent is selected from the group consisting of: polyethylene glycol, an antibody, a half antibody, an antibody fragment, a fluorescent probe, an aptamer, a vitamin, a cell surface receptor, a cell coat, a protein, a peptide, a radioactive isotope, a contrast media, a surface charge modifier, a lectin, and combinations thereof.

36. The nanocomposite of claim 29, further comprising an antibody or an antibody fragment bound to said linker bound to said functional group of said nanocomposite.

37. The nanocomposite of claim 36, wherein said antibody or an antibody fragment bound to said linker bound to said functional group of said nanocomposite adapted to bind a cellular target.

38. The nanocomposite of claim 37, wherein said antibody or said antibody fragment bound to said linker bound to said functional group of said nanocomposite adapted specifically bind said cellular target.

39. The nanocomposite of claim 38, wherein said antibody or antibody fragment bound to said linker bound to said functional group of said nanocomposite adapted to bind said cellular target without detectable non-specific binding of other molecules.

40. The nanocomposite of claim 37, wherein said nanocomposite linked to said antibody or antibody fragment bound to said cellular target is analyzed by flow cytometry for detection of said cellular target.

41. The nanocomposite of claim 37, further comprising a magnetic field wherein said nanocomposite linked to said antibody or antibody fragment binding said cellular target is placed in a magnetic field to isolate said nanocomposite linked to said antibody or antibody fragment binding said cellular target.

42. The nanocomposite of claim 41, wherein said nanocomposite linked to said antibody or antibody fragment binding said cellular target isolated by placement in said magnetic field analyzed by flow cytometry for detection of said cellular target.

43. The nanocomposite of claim 36, wherein said antibody or antibody fragment comprises mouse anti human CD3 and a cellular target comprises a human CD3 peripheral blood mononuclear cells.

44. The nanocomposite of claim 36, wherein said antibody or antibody fragment comprises mouse anti human CD4 and a cellular target comprises a human CD4 peripheral blood mononuclear cell.

45. The nanocomposite of claim 43, wherein said nanocomposite linked to said mouse anti human CD3 binding said human CD3 peripheral blood mononuclear cell is analyzed by flow cytometry for detection of human CD3-peripheral blood mononuclear cell.

46. The nanocomposite of claim 45, wherein said nanocomposite linked to said mouse anti human CD3 binding said human CD3 peripheral blood mononuclear cell is detected by flow cytometry flow sorted into an isolated population of said nanocomposite linked to said mouse anti human CD3 binding said human CD3 peripheral blood mononuclear cell.

47. The nanocomposite of claim 44, wherein said nanocomposite linked to said mouse anti human CD4 binding said human CD4 peripheral blood mononuclear cell is analyzed by flow cytometry for detection of human CD4 peripheral blood mononuclear cell.

48. The nanocomposite of claim 47, wherein said nanocomposite linked to said mouse anti human CD4 binding said human CD4 peripheral blood mononuclear cell is detected by flow cytometry flow sorted into an isolated population of said nanocomposite linked to said mouse anti human CD4 binding said human CD4 peripheral blood mononuclear cell.

49. The nanocomposite of claim 44, wherein said nanocomposite linked to said mouse anti human CD3 binding said human CD3 peripheral blood mononuclear cell is isolated under influence of a magnetic field.

50. The nanocomposite of claim 49, wherein said nanocomposite linked to said mouse anti human CD3 binding said human CD3 peripheral blood mononuclear cell isolated by influence of said magnetic field analyzed by flow cytometry for detection of human CD3-peripheral blood mononuclear cell.

51. The nanocomposite of claim 50, wherein said nanocomposite linked to said mouse anti human CD3 binding said human CD3 peripheral blood mononuclear cell is detected by flow cytometry flow sorted into an isolated population of said nanocomposite linked to said mouse anti human CD3 binding said human CD3 peripheral blood mononuclear cell.

52. The nanocomposite of claim 44, wherein said nanocomposite linked to said mouse anti human CD4 binding said human CD4 peripheral blood mononuclear cell is isolated under influence of a magnetic field.

53. The nanocomposite of claim 52, wherein said nanocomposite linked to said mouse anti human CD4 binding said human CD4 peripheral blood mononuclear cell is isolated under influence of a magnetic field detected by flow cytometry for detection of said human CD4 peripheral blood mononuclear cell.

\* \* \* \* \*

UNITED STATES PATENT AND TRADEMARK OFFICE
CERTIFICATE OF CORRECTION

| | | |
|---|---|---|
| PATENT NO. | : 12,370,266 B2 | Page 1 of 1 |
| APPLICATION NO. | : 17/943788 | |
| DATED | : July 29, 2025 | |
| INVENTOR(S) | : Kristie Marie Krug and Mythreyi Unni | |

It is certified that error appears in the above-identified patent and that said Letters Patent is hereby corrected as shown below:

In the Claims

In Column 31, Line 5 (Claim 2, Line 5) "at least one quantum" should read --at least one quantum dot--.

In Column 31, Line 11 (Claim 3, Line 5) "at least one quantum" should read --at least one quantum dot--.

In Column 31, Line 18 (Claim 4, Line 6) "at least one quantum" should read --at least one quantum dot--.

In Column 31, Line 24 (Claim 5, Line 5) "at least one quantum" should read --at least one quantum dot--.

In Column 31, Line 31 (Claim 6, Line 6) "at least one quantum" should read --at least one quantum dot--.

In Column 31, Line 39 (Claim 7, Line 6) "at least one quantum" should read --at least one quantum dot--.

In Column 31, Line 46 (Claim 8, Line 6) "at least one quantum" should read --at least one quantum dot--.

Signed and Sealed this
Twenty-sixth Day of August, 2025

Coke Morgan Stewart
*Acting Director of the United States Patent and Trademark Office*